US007829662B2

(12) United States Patent
Korsmeyer et al.

(10) Patent No.: US 7,829,662 B2
(45) Date of Patent: Nov. 9, 2010

(54) METHOD OF TREATING APOPTOSIS AND COMPOSITIONS THEREOF

(75) Inventors: Stanley J. Korsmeyer, Weston, MA (US); Luca Scorrano, Padova (IT)

(73) Assignee: Dana Farber Cancer Institute, Inc., Boston, MA (US)

( * ) Notice: Subject to any disclaimer, the term of this patent is extended or adjusted under 35 U.S.C. 154(b) by 39 days.

(21) Appl. No.: 11/818,915

(22) Filed: Jun. 15, 2007

(65) Prior Publication Data

US 2008/0097081 A1 Apr. 24, 2008

Related U.S. Application Data

(62) Division of application No. 10/334,006, filed on Dec. 30, 2002, now Pat. No. 7,247,700.

(60) Provisional application No. 60/345,733, filed on Dec. 31, 2001, provisional application No. 60/382,207, filed on May 21, 2002.

(51) Int. Cl.
*C07K 5/10* (2006.01)
(52) U.S. Cl. ...................... 530/300; 530/327
(58) Field of Classification Search .................. None
See application file for complete search history.

(56) References Cited

U.S. PATENT DOCUMENTS 5,955,593 A 9/1999 Korsmeyer
6,747,137 B1 * 6/2004 Weinstock et al. ......... 536/23.1

FOREIGN PATENT DOCUMENTS

WO WO 99/46371 9/1999

OTHER PUBLICATIONS

Bernardi and Azzone (1981). J Biol Chem 256: 7187-7192.
Bernardi (1999). Physiol Rev 79: 1127-1155.
Cheng, et al. (2001). Mol Cell 8: 705-711.
Clipstone and Crabtree (1992). Nature 357: 695-697.
Eskes, et al. (1998). J Cell Biol 143: 217-224.
Frank, et al. (2001). Dev Cell 1: 515-525.
Frey and Mannella (2000): Trends Biochem Sci 25: 319-324.
GenBank Accession No. NM_001196; Apr. 3, 2003.
GenBank Accession No. NM_022684; Apr. 6, 2003.
GenBank Accession No. NM_007544; Apr. 7, 2003.
Goldstein et al. (2000). Nat Cell Biol 2: 156-162.
Green and Reed (1998) Science 281: 1309-1312.
Hackenbrock (1966). J Cell Biol 30: 269-297.
Hajek, et al. (2001). J Biol Chem 276: 606-615.
Hengartner and Horvitz (1994). Cell 76: 1107-1114.
Huser, et al. (1998). Biophys J 74: 2129-2137.
Kluck, et al. (1999). J Cell Biol 147: 809-822.
Kroemer, et al. (1998). Annu Rev Physiol 60: 619-642.
Lehninger (1951). J Biol Chem 190: 345-359.
Lemasters, et al. (1998). Biochim Biophys Acta 1366: 177-196.
Li, et al. (1997). Cell 91: 479-489.
Luo, et al. (1998). Cell 94: 481-490.
Mancini, et al. (1997). J Cell Biol 138: 449-469.
Mannella, et al. (2001). IUBMB Life 52(3-5): 93-100.
Margolin (2000). Curr Biol 10: R328-R330.
Marko and Leith (1996). J Struct Biol 116: 93-98.
Nicholls, et al. (1980). Can J Biochem 58: 969-977.
Nicolli, et al. (1996). J Biol Chem 271: 2185-2192.
Oltvai and Korsmeyer (1994). Cell 79: 189-192.
Penczek, et al. (1995). Ultramicroscopy 60: 393-410.
Perotti, et al. (1983). J Histochem Cytochem 31: 351-365.
Petronilli, et al. (1989). FEBS Lett 259: 137-143.
Petronilli, et al. (1999). Biophys J 76: 725-734.
Radermacher (1992). In Electron Tomography: 91-115.
Raff (1992). Nature 356: 397-400.
Sheridan, et al. (1981). J Cell Sci 49: 119-137.
Shimizu and Tsujimoto (2000). Proc Natl Acad Sci USA 97: 577-582.
Single, et al. (1998). Cell Death Differ 5: 1001-1003.
von Ahsen, et al. (2000). J Cell Biol 150: 1027-1036.
Wei, et al. (2000). Genes Dev 14: 2060-2071.
Wei, et al. (2001). Science 292: 727-730.
Zong, et al. (2001). Genes Dev 15: 1481-1486.
Zoratti and Szabo (1995). Biochim Biophys Acta 1241: 139-176.
Zha, et al. (2000). Science 290: 1761-1765.
Eskes et al. *Mol. Cell. Biol.*, 20(3):929-935 (2000).
Esposti, M.D., *Apoptosis*, 7(5):433-440 (2002).
Hu et al. *Apoptosis*, 8(3):277-289 (2003).
Letai et al. *Cancer Cell*, 2(3):183-192 (2002).
Liu et al. *Biochem. Biophys. Res. Commun.*, 330(3):865-870 (2005).
Lutter et al. *Nat. Cell Biol.*, 2(10):754-756 (2000).
Scorrano et al. *Dev. Cell*, 2(1):55-67 (2002).
Wang et al. *Genes Dev.*, 10(22):2859-2869 (1996).
Zhai et al. *Eur. J. Biochem.*, 268(1):48-55 (2001).
Partial European Search Report for EP 02 79 9347, mailed Jul. 26, 2006.
Medline (Database on STN) Accession No. 94101555.
International Search Report for PCT/US02/041789 mailed Sep. 8, 2003.

\* cited by examiner

*Primary Examiner*—Misook Yu
*Assistant Examiner*—Mark Halvorson
(74) *Attorney, Agent, or Firm*—Mintz Levin Cohn Ferris Glovsky and Popeo, P.C.; Ivor R. Elrifi, Esq.; Cynthia A. Kozakiewicz

(57) ABSTRACT

Disclosed herein are novel polypeptides and the nucleic acid sequences that encode them. Also disclosed are antibodies that immunospecifically bind to the polypeptide, as well as derivatives, variants, mutants, or fragments of the novel polypeptide, polynucleotide, or antibody specific to the polypeptide. Vectors, host cells, antibodies and recombinant methods for producing the polypeptides and polynucleotides, as well as methods for using same are also included. The invention further discloses therapeutic, diagnostic and research methods for diagnosis, treatment, and prevention of apoptosis associated disorders involving these novel human nucleic acids and proteins.

4 Claims, 20 Drawing Sheets

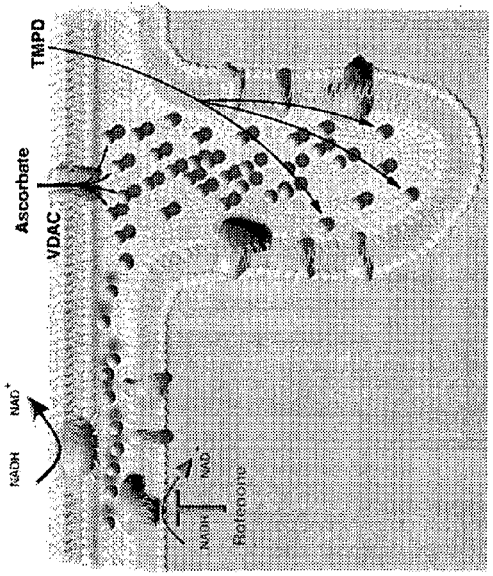
FIG. 3A
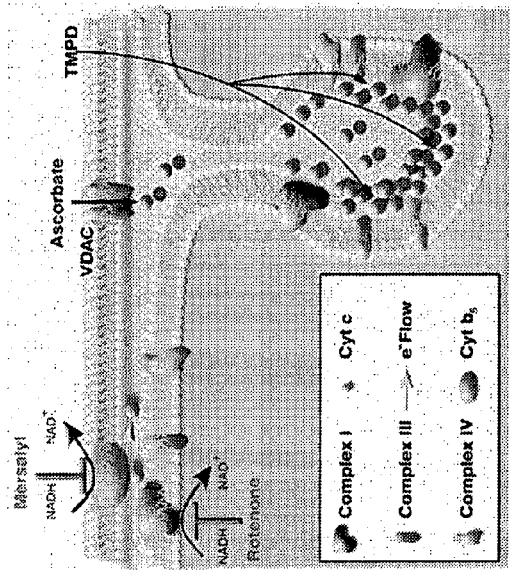
FIG. 3B
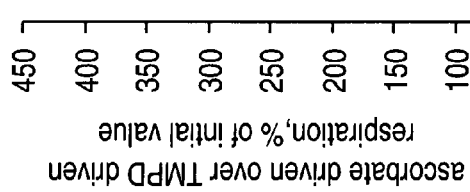
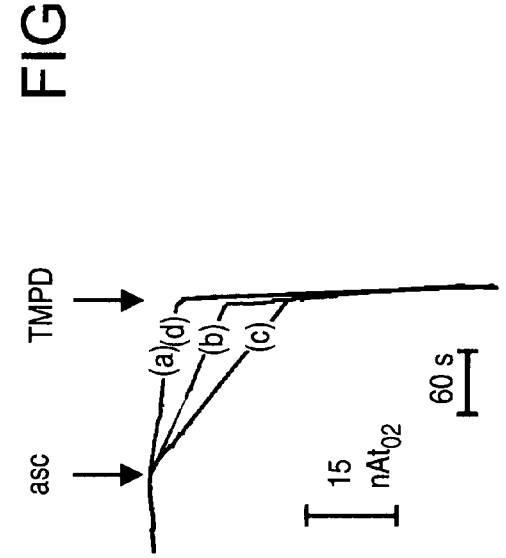
FIG. 3C
FIG. 3D

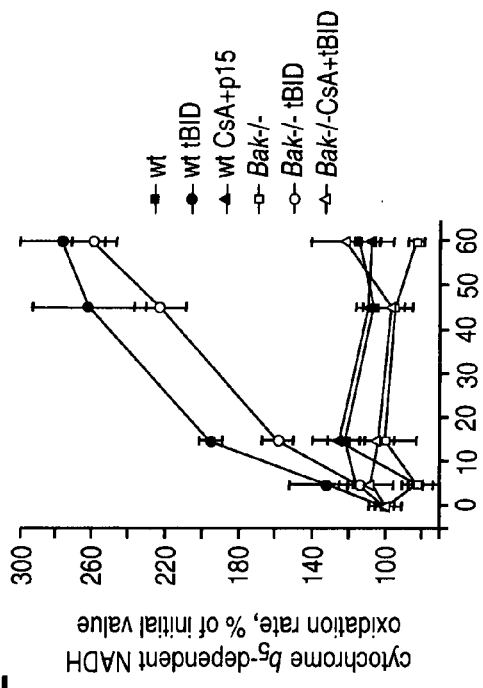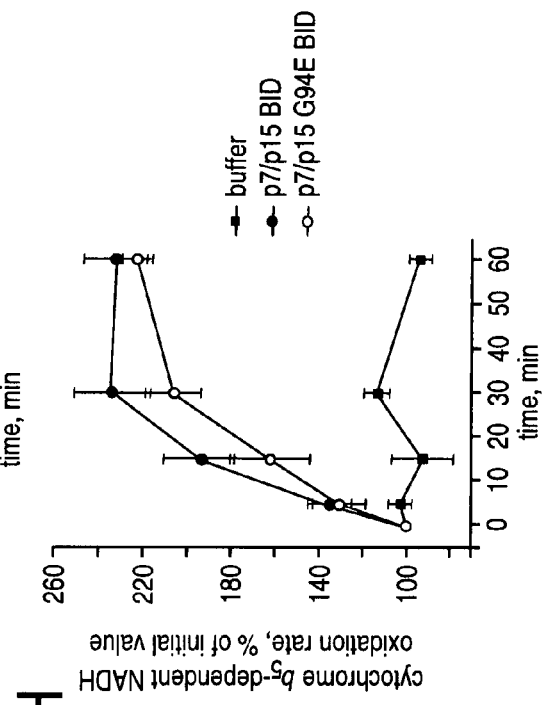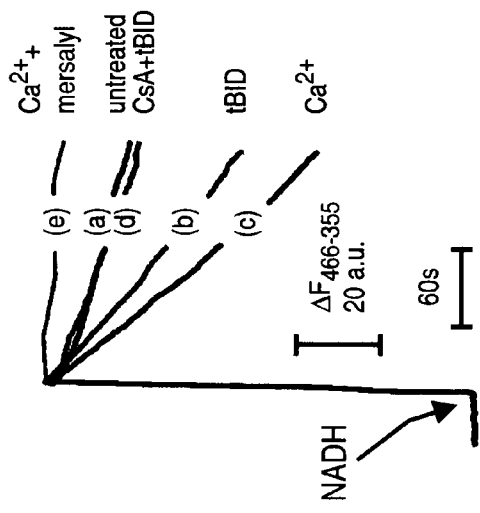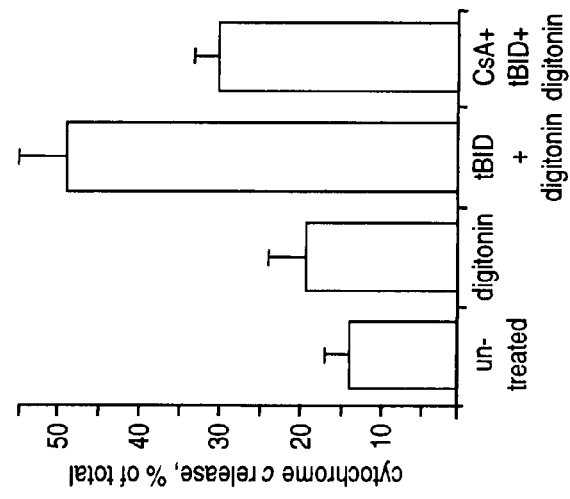
FIG. 3E
FIG. 3F
FIG. 3G
FIG. 3H

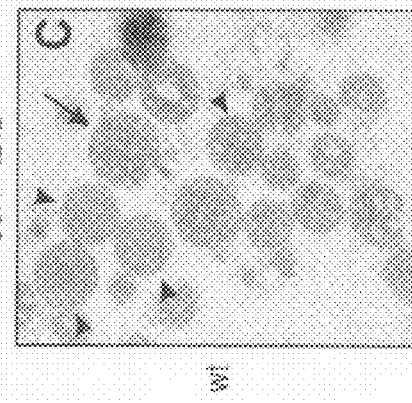
FIG. 4A wt
FIG. 4B tBID wt
FIG. 4C CsA+tBID wt
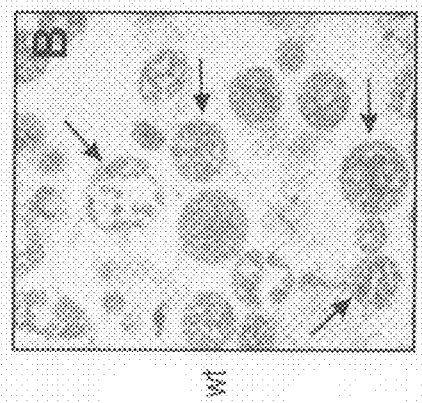
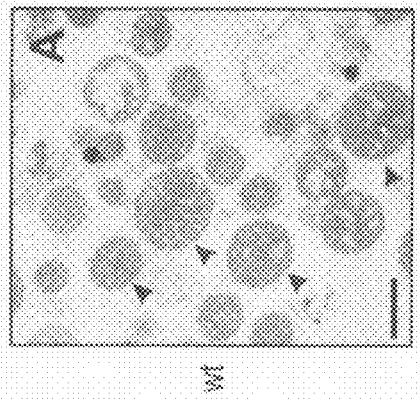
FIG. 4D Bak -/-
FIG. 4E tBID Bak -/-
FIG. 4F CsA+tBID Bak -/-
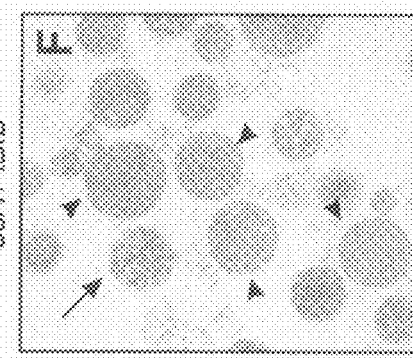
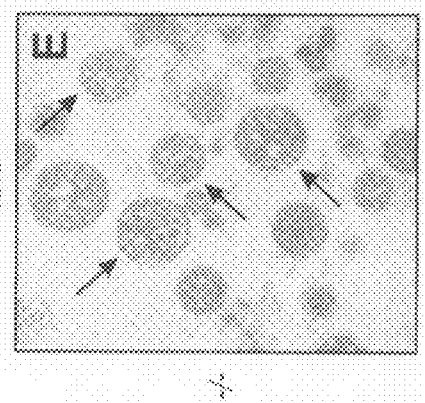
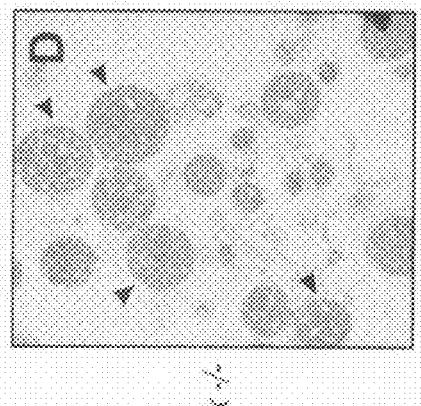

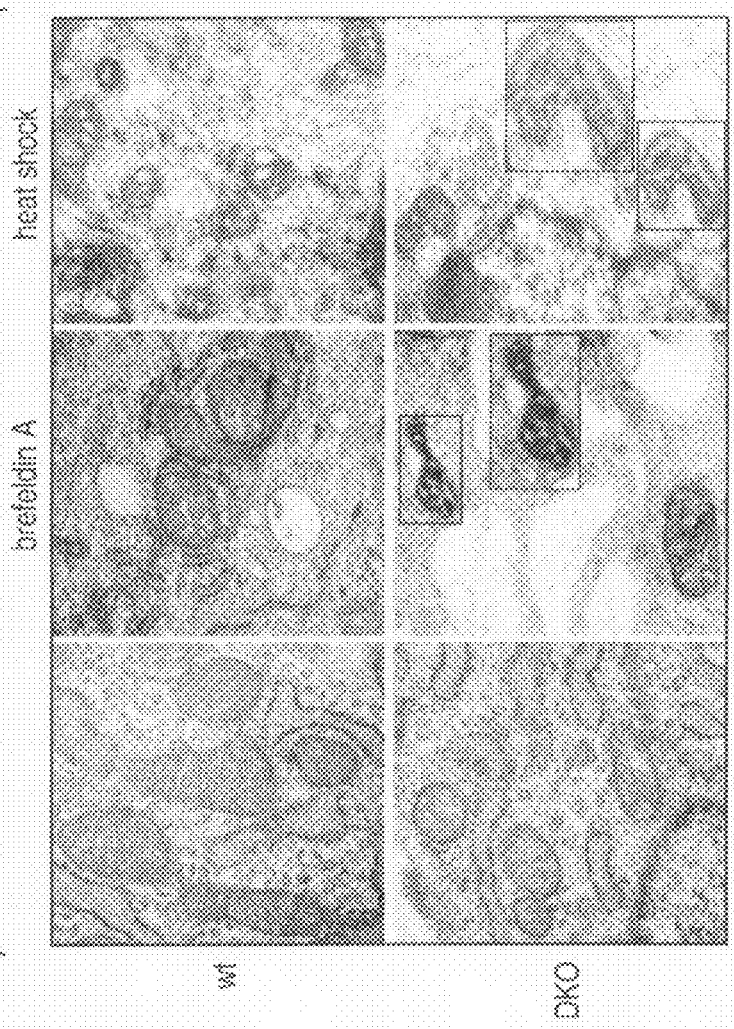
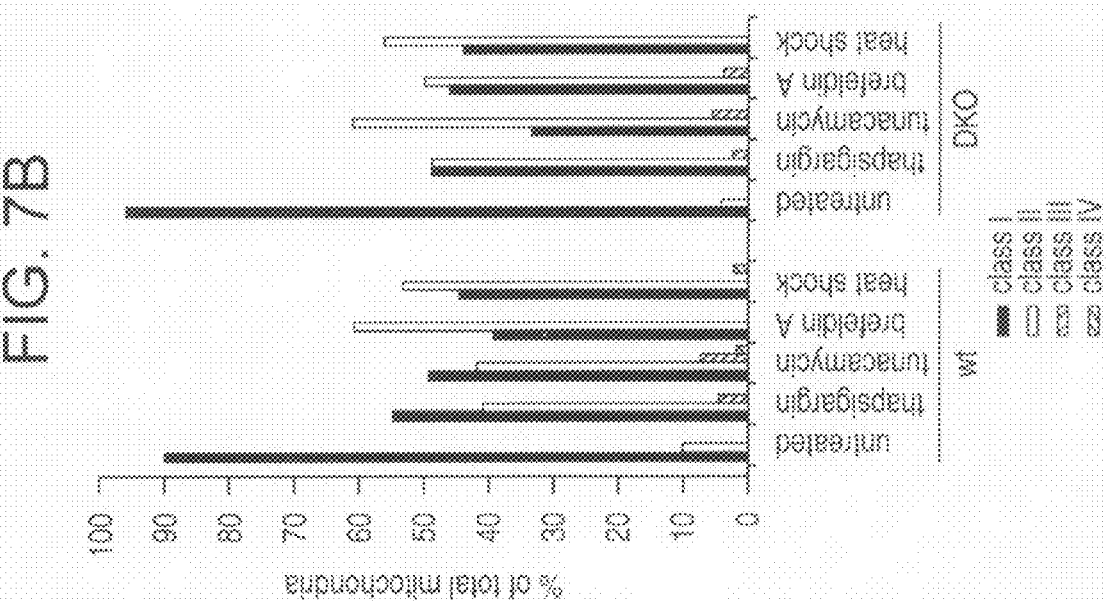
FIG. 7A
FIG. 7B

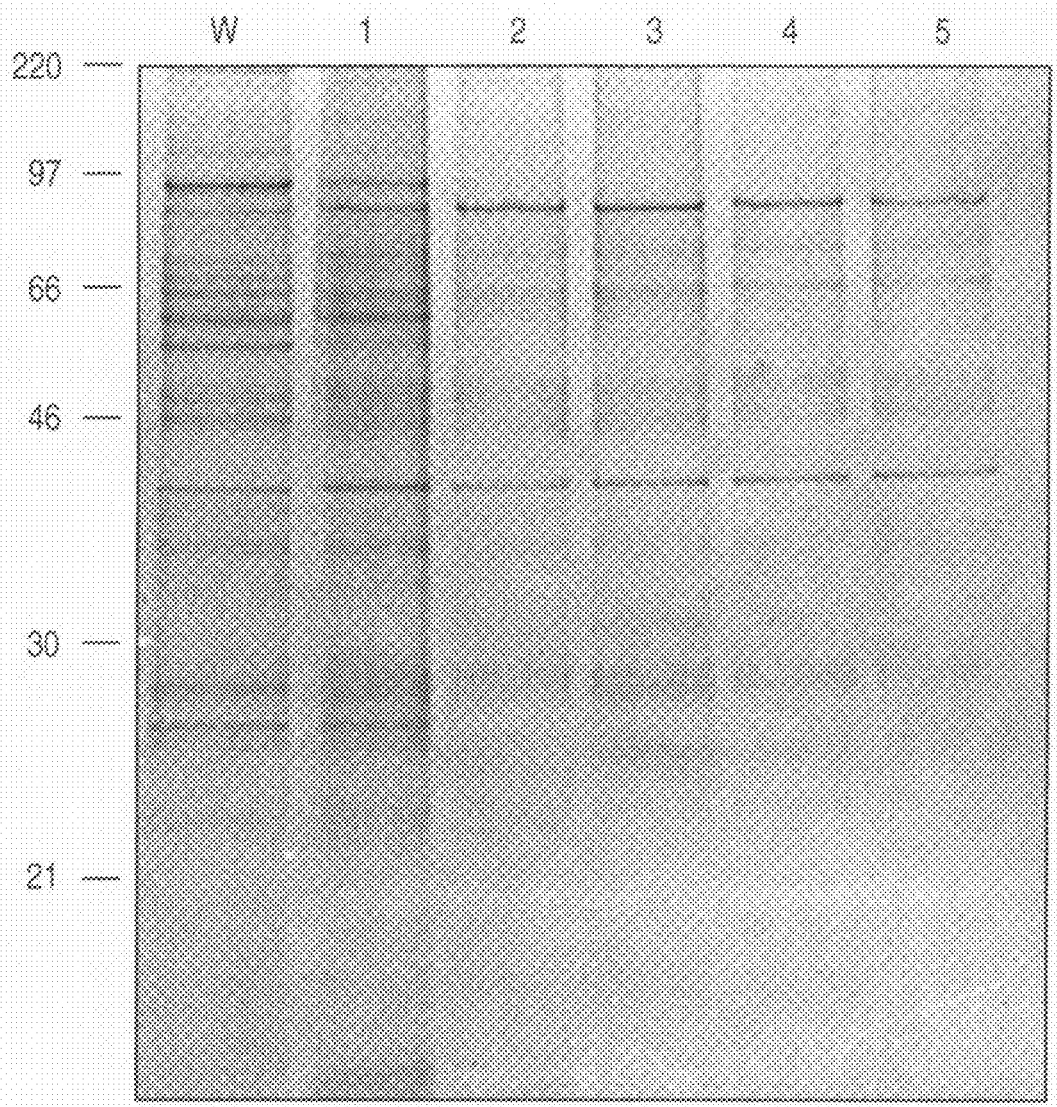

METHOD OF TREATING APOPTOSIS AND COMPOSITIONS THEREOF

RELATED APPLICATIONS

This application is a divisional application of U.S. Ser. No. 10/334,006, filed Dec. 30, 2002, now U.S. Pat. No. 7,247,700, which claims priority to U.S. Ser. No. 60/345,733, filed Dec. 31, 2001, and U.S. Ser. No. 60/382,207, filed May 21, 2002. Each of these references is incorporated herein by reference in its entirety.

STATEMENT AS TO FEDERALLY SPONSORED RESEARCH

This invention was made with U.S. government support under NIH grants CA50239-14 and RR01219. The government has certain rights in the invention.

FIELD OF THE INVENTION

This invention relates generally to methods and compositions for the regulation of apoptosis. It also relates to the novel death agonist, BID, polypeptide variants of BID, and the polynucleotides encoding them.

BACKGROUND OF THE INVENTION

Programmed cell death, referred to as apoptosis, plays an indispensable role in the development and maintenance of tissue homeostasis within all multicellular organisms (Raff, Nature 356: 397-400, 1992). Genetic and molecular analysis from nematodes to humans has indicated that the apoptotic pathway of cellular suicide is highly conserved (Hengartner and Horvitz, Cell 76: 1107-1114, 1994). In addition to being essential for normal development and maintenance, apoptosis is important in the defense against viral infection and in preventing the emergence of cancer.

Considerable progress has been made in identifying molecules that regulate the apoptotic pathway at each level. Of note, both positive and negative regulators, often encoded within the same family of proteins, characterize the extracellular, cell surface and intracellular steps (Oltvai and Korsmeyer, Cell 79: 189-192, 1994).

The mitochondrion is a highly complex and compartmentalized organelle and is a prominent participant in apoptosis following a variety of death stimuli (Green and Reed, Science 281, 1309-1312, 1998; Kroemer et al., Annu. Rev. Physiol. 60, 619-642, 1998). The "multidomain" pro-apoptotic BCL-2 family members BAX and BAK prove necessary for the onset of mitochondrial dysfunction and cell death following remarkably diverse signals (Wei et al., Science 292, 727-730, 2001). Thus, mitochondria may prove an obligate organelle for apoptosis downstream of perhaps all intrinsic pathway signals. Release of cytochrome c from the intermembrane space (IMS) is a prominent facet of such intrinsic pathway deaths. Cytochrome c triggers a post mitochondrial pathway, forming an "apoptosome" of Apaf-1, cytochrome c and caspase-9 which subsequently cleaves the effector caspases-3,-7 (Li et al., Cell 91, 479-489, 1997).

The precise mechanism whereby cytochrome c is released across the outer mitochondrial membrane (OM) is less certain. Permeability transition (PT) that ultimately leads to mitochondrial swelling with secondary rupture of the OM and cytochrome c release has been noted in certain apoptotic and necrotic deaths (Lemasters et al., Biochim. Biophys. Acta 1366, 177-196, 1998). In its fully open conformation the PT pore (PTP), a high conductance inner membrane channel, is permeable to solutes up to 1500 Da (Bernardi, Physiol. Rev. 79, 1127-1155, 1999). However, openings of the PTP can also be transient and not cause swelling (Huser et al., Biophys. J. 74, 2129-2137, 1998; Petronilli et al., Biophys. J. 76, 725-734, 1999). As originally noted at the single channel level, the PTP flickers over milliseconds (msecs) between its open and closed states (Petronilli et al., FEBS Lett. 259, 137-143, 1989). Cyclosporin A (CsA) inhibits both activities of the PTP, presumably through its mitochondrial target cyclophilin D (Nicolli et al., J. Biol. Chem. 271, 2185-2192, 1996). Thus, models of cytochrome c release must also assess whether PT participates.

Defining the serial events responsible for cytochrome c release requires a distinct initiating event. The "BH3 domain-only" subset of BCL-2 members provides such a signal as they connect proximal death signals to the core apoptotic pathway at the mitochondria. The "BH3 domain-only" molecules BID, BAD, BIM, NOXA require the "multidomain" members BAX, BAK to release cytochrome c and induce cell death (Wei et al., 2001; Zong et al., Genes Dev. 15, 1481-1486, 2001; Cheng et al., Mol. Cell. 8, 705-711, 2001). For example, after CD95 (Fas) or TNFR1 engagement BID is cleaved by caspase-8 followed by N-myristoylation to induce its molecular activation (Luo et al., Cell 94, 481-490, 1998; Zha et al., Science 290, 1761-1765, 2000). Recombinant tBID (truncated p15 BID) is an ideal initiating event as it appears to function as a death ligand that induces the homo-oligomerization of BAK with subsequent release of cytochrome c from wild-type (wt) but not Bak-deficient mitochondria (Wei et al., Genes Dev. 14, 2060-2071, 2000). tBID releases cytochrome c without detectable swelling of the mitochondria (Shimizu and Tsujimoto, Proc. Natl. Acad. Sci. U.S.A. 97, 577-582, 2000; Eskes et al., J. Cell Biol. 143, 217-224, 1998; Wei et al, 2000) but increases the permeability of the OM (Kluck et al., J. Cell Biol. 147, 809-822, 1999).

Any model must also account for the rapid kinetics and complete extent of cytochrome c release (Goldstein et al., Nat. Cell Biol. 2, 156-162, 2000). High-voltage electron microscopic (HVEM) tomography of mitochondria has revealed that the IMS is very narrow, as the average distance between the OM and inner boundary membranes (IM) is only ~20 nm (Frey and Manila, Trends. Biochem. Sci. 25, 319-324, 2000) consistent with functional estimates that only 15-20% of total cytochrome c is available in the IMS (Bernardi and Azzone, J. Biol. Chem. 256, 7187-7192, 1981). The pleomorphic, tubular cristae constitute highly sequestered compartments where the majority of oxidative phosphorylation complexes (Perotti et al., J. Histochem. Cytochem. 31, 351-365, 1983) and cytochrome c are located. Cristae junctions of ~18 nm diameter physically separate the tubular cristae compartments from the narrow IMS in normal liver mitochondria. The major stores of cytochrome c (~85%) are sequestered within the cristae, and computer modeling of this subcompartmentalization indicates ion and ADP diffusion gradients across the cristae junctions (Mannella et al., IUBMB Life, 52(3-5):93-100, 2001). A major challenge is to explain how this compartmentalized store of cytochrome c can be released in the absence of mitochondrial swelling. Therefore, investigating whether a structural reorganization occurs during apoptosis to mobilize the cristae stores of cytochrome c for release across the OM is desirable.

Some disease conditions are affected by the development of a defective apoptotic response. For example, neoplasias may result, at least in part, from an apoptosis-resistant state in which cell proliferation signals inappropriately exceed cell death signals. Furthermore, some DNA viruses such as Epstein-Barr virus, African swine fever virus and adenovirus, parasitize the host cellular machinery to drive their own replication and at the same time modulate apoptosis to repress cell death and allow the target cell to reproduce the virus. Moreover, certain disease conditions such as lymphoproliferative conditions, cancer including drug resistant cancer, arthritis, inflammation, autoimmune diseases and the like may result from a defect in cell death regulation. In such disease conditions, it would be desirable to promote apoptotic mechanisms.

Furthermore, in certain disease conditions it would be desirable to inhibit apoptosis such as in the treatment of immunodeficiency diseases, including AIDS, senescence, neurodegenerative diseases, ischemia and reperfusion, infertility, wound-healing, and the like. In the treatment of such diseases it would be desirable to diminish or inhibit cell death agonist activity.

Since there is an unmet need in regard to apoptotic modulation, it is desirable to identify novel proteins or critical protein domains which have cell-death agonist/antagonist properties and to utilize these as a basis for treatment modalities in advantageously modulating the apoptotic process in disease conditions involving either inappropriate repression or inappropriate enhancement of cell death.

SUMMARY OF THE INVENTION

The present invention is based on the discovery that the cell-death agonist, BID (BH3 Interacting Domain Death Agonist), and more specifically, the BID α6 helix domain, is critical for modulating mitochondrial remodeling, the release of cytochrome c stored in mitochondrial cristae and apoptosis.

Accordingly, in one embodiment, the invention provides an amino acid sequence of a BID α6 14mer which does not dimerize with BAX, BCL-2 or BCL-X. The BID α6 14mer can be the peptide of SEQ ID NOs:1-3.

In another embodiment, the invention provides a BID mutein polypeptide which is at least 85% similar to wild type BID. The BID mutein polypeptide can display decreased triggering of cytochrome c release from mitochondria compared to wild type BID. The BID mutein polypeptide can have an amino acid at position 157, numbered in accordance with wild type BID, which is not a lysine residue. The BID mutein polypeptide can have an amino acid at position 158, numbered in accordance with wild type BID, which is not a lysine residue. The BID mutein polypeptide can have an alanine amino acid at position 157. The BID mutein polypeptide can have an alanine amino acid at position 158.

In another embodiment, the invention provides a BID α6 mutein amino acid sequence of SEQ ID NOs:7-9. The BID α6 mutein cannot dimerize with BAX, BCL-2 or BCL-X.

In another embodiment, the invention provides a nucleic acid encoding for a BID α6 14mer, BID α6 mutein or fragment thereof.

In another embodiment, the invention provides an expression vector containing a nucleic acid encoding for a BID α6 14mer, BID α6 mutein or fragment thereof and a host cell containing the expression vector. The host cell can be a eukaryotic cell or a prokaryotic cell.

In another embodiment, the invention provides a pharmaceutical composition that includes a BID α6 polypeptide, BID α6 mutein or fragment thereof and a pharmaceutically acceptable carrier. The invention also provides a pharmaceutical composition that includes a nucleic acid encoding for a BID α6 polypeptide, BID α6 mutein or fragment thereof and a pharmaceutically acceptable carrier.

In another embodiment, the invention provides an antibody that binds specifically to a BID α6 polypeptide, BID α6 mutein or fragment thereof. The antibody can be, e.g., monoclonal, polyclonal or humanized.

In another embodiment, the invention provides a method for treating or preventing an apoptosis-associated disorder by administering to the subject in need a therapeutically effective amount of a BID α6-inhibitor (an inhibitor of the effector activity of BID α6) to inhibit apoptosis. The BID α6-inhibitor can be, e.g., a cyclosporin compound, cyclosporin A, suramin, BID α6 mutein or a BID α6 helix variant peptide that lacks cytochrome c release activity. The cyclosporin compound can modulate cyclophilin D. The BID α6-inhibitor can also be an antibody or antibody fragment which binds to a BID α6 helix peptide or fragment thereof. The antibody can be, e.g., monoclonal or humanized. The BID α6-inhibitor can be administered with a caspase inhibitor. The caspase inhibitor can be, e.g., an active peptide fragment of human cytochrome b, human Tat binding protein, human mitochondrial loop attachment site, a glutamate-binding subunit of a human NMDA receptor complex, human myelin basic protein, human synaptophysin p38, human snRNP protein B, human protein 1, human ubiquitin C-terminal hydrolase, human tissue inhibitor of metalloprotease-3, human MHC HLA-DRw12-MHC class II beta chain, human transglutaminase, human death associated protein 1, human hnRNP D, viral protein p35, or synthetic peptides z-VAD-fmk, IETD/fmk, CrmA, AC-DEVD-fmk, YVAD-cmk, or z-DEVD-fmk. The disorder can be, e.g., a neurodegenerative disorder, any degenerative disorder, an immunodeficiency disorder, an acute ischemic injury or infertility. The immunodeficiency disorder can be AIDS/HIV.

In another embodiment, the invention provides a method for inducing apoptosis in a subject by administering to the subject in need a BID α6-stimulator in an amount effective to induce apoptosis. The BID α6-stimulator can be, e.g., an effective amount of a BID α6 helix polypeptide, a nucleic acid encoding for a BID α6 helix polypeptide or a fragment thereof. The BID α6-stimulator can be administered with a anti-angiogenic compound. The anti-angiogenic compound can be, e.g., a tyrosine kinase inhibitor, an epidermal-derived growth factor inhibitor, a fibroblast-derived growth factor inhibitor, a platelet-derived growth factor inhibitor, a matrix metalloprotease (MMP) inhibitor, an integrin blocker, interferon alpha, interferon-inducible protein 10, interleukin-12, pentosan polysulfate, a cyclooxygenase inhibitor, a nonsteroidal anti-inflammatory (NSAID), a cyclooxygenase-2 inhibitor, carboxyamidotriazole, tetrahydrocortisol, combretastatin A-4, squalamine, 6-O-chloroacetyl-carbonyl)-fumagillol, thalidomide, angiostatin, endostatin, troponin-1, an antibody to VEGF, platelet factor 4 or thrombospondin. The BID α6-stimulator can be administered with a chemotherapeutic compound. The chemotherapeutic compound can be paclitaxel, taxol, lovastatin, minosine, tamoxifen, gemcitabine, 5-fluorouracil (5-FU), methotrexate (MTX), docetaxel, vincristine, vinblastin, nocodazole, teniposide, etoposide, adriamycin, epothilone, navelbine, camptothecin, daunonibicin, dactinomycin, mitoxantrone, amsacrine, epirubicin or idarubicin. The BID α6-stimulator can include a tissue targeting moiety. The tissue targeting moiety can be an antibody. The subject can be susceptible to a disorder, e.g., cancer or an autoimmune disorder.

In another embodiment, the invention provides a method of inhibiting apoptosis in a cell by contacting the cell with a BID α6-inhibitor, in an amount sufficient to inhibit apoptosis. The BID α6-inhibitor can be, e.g., a cyclosporin, cyclosporin A, suramin, BID α6 mutein, a non-functional BID α6 helix variant or an antibody that binds to a BID α6 helix peptide or fragment thereof. The cell can be provided in vitro, in vivo or ex vivo.

In another embodiment, the invention provides a method of inducing apoptosis in a cell by contacting the cell with a BID α6-stimulator compound, in an amount sufficient to induce apoptosis. The BID α6-stimulator compound can be, e.g., a BID α6 polypeptide, a nucleic acid encoding for a BID α6 polypeptide or fragment thereof. The BID α6 polypeptide can be the BID α6 14mer which does not dimerize with BAX, BCL-2 or BCL-X or the BID α6 14mer of SEQ ID NOs:1-3. The cell can be provided in vitro, in vivo or ex vivo.

In another embodiment, the invention provides a method for screening for BID α6-inhibitor compounds by contacting a cell with a candidate compound, measuring apoptosis, if present, and determining the ability of the candidate compound to inhibit apoptosis by measuring a decrease of apoptosis in the presence of the compound as compared to absence of the compound. Also within the invention is a BID α6-inhibitor compound identified by the screening method.

In another embodiment, the invention provides a method for screening for BID α6-stimulator compound by contacting a cell with a candidate compound, measuring apoptosis, if present, and determining the ability of the candidate compound to stimulate apoptosis by measuring an increase of apoptosis in the presence of the compound as compared to absence of the compound. Also within the invention is a BID α6-stimulator compound identified by the screening method.

In another embodiment, the invention provides a method for detecting a BID associated protein by providing a cellular component, contacting the cellular component with an immobilized BID protein, collecting a BID associated cellular component thereby identifying a BID associated protein. The immobilized BID protein can be p7/p15 caspase 8 cleaved BID or tBID. The BID associated protein can be identified by Western blot analysis or Mass spectrometry. Also within the invention is a BID associated protein identified by the screening method.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

FIG. 3 is a schematic representation and corresponding bar and line graphs showing the effects of BID on cytochrome c mobilization in wt and Bak −/− mitochondria.

FIG. 4 is a photograph of a transmission electron micrograph (TEM) showing tBID treated wt and Bak −/− mitochondria.

FIG. 7 is a photograph of a transmission electron micrograph and corresponding bar graphs showing mitochondrial morphology and morphometry in Wt and Bax, Bak-deficient cells primed for apoptosis.

FIG. 19 is a photograph of a silver stained gel showing a pattern of mitochondrial proteins interacting with BID α6 helix.

DETAILED DESCRIPTION OF THE INVENTION

Figure 1A:
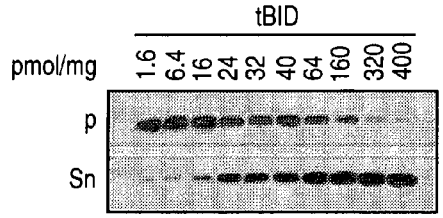
FIG. 1 is a photograph of a Western blot and corresponding line graphs showing tBID induced cytochrome c release and effects on light scattering, mitochondrial membrane potential, and calcein release.

The present invention is based in part on the discovery that peptides comprising the α6 helix domain of wild-type BH3 Interacting Domain Death Agonist (wt BID), and not the BH3 domain, are responsible for cytochrome c mobilization and remodeling of the mitochondrial inner membrane. The peptides of the invention are referred to herein as BID α6 peptides and BID muteins. Additionally, the invention provides methods and pharmaceutical compositions for treating pathophysiologies associated with apoptosis, e.g., cell proliferative disorders.

As used herein, "wt BID" means any wild-type BID, whether native or recombinant, having the naturally occurring amino acid sequence of the full-length, native BID, as shown in, e.g., U.S. Pat. No. 5,955,593; GenBank Accession Nos: NM_001196, NM_007544, or NM_022684.

wt BID polypeptides are able to interact with both death agonists and death antagonists of the BCL-2 family. wt BID acts as a death agonist through its ability to heterodimerize with the death agonist BAX and, alternatively, acts as a death antagonist by heterodimerizing with the death antagonists BCL-2 and BCL-$X_L$. The characteristics of wt BID suggest a model in which agonists (BAX) or antagonists (BCL-2) represent membrane bound receptors that compete for a common ligand, BID.

wt BID contains a BH3 domain which is required for wt BID to bind to members of the BCL-2 family. The BH3 domain is a BCL-2 homology α3-helical domain which is essential for heterodimerization and killing activity in other members of the BCL-2 family. wt BID is present in the cell in two distinct isoforms. The first isoform is termed p22 BID and resides in the cytoplasm. p22 BID is activated by caspase-8 cleavage and this cleavage results in a truncated p15 BID protein product termed tBID. Following cleavage, tBID translocates to the mitochondria where it inserts into the mitochondrial membrane and functions to release cytochrome c from the mitochondria and initiate an apoptosis pathway (Wei et al., 2000).

BID α6 Polypeptides

In one aspect, the invention provides a BID α6 peptide. No particular length is implied by the term "peptide". In some embodiments, the BID α6 peptide is less than 195 amino acids in length, e.g., less than or equal to 150, 100, 75, 50, 35, 25 or 15 amino acid in length. In various embodiments, the BID α6 peptide includes the amino acid sequence of SEQ ID NO: 1-3 where the peptide does not dimerize with BAX, BCL-2 or BCL-$X_L$. In another embodiment, the BID α6 peptide is capable of mitochondrial inner membrane remodeling and cytochrome c mobilization. In a further embodiment, the BID α6 peptide stimulates apoptosis.

Examples of BID α6 peptides include a peptide which includes (in whole or in part) the sequence NH$_2$-XM-LXXXXLLAKKVA—COOH (SEQ ID NO:1). As used herein X may be any amino acid. In another embodiment, the peptide includes the sequence NH$_2$-TMLVLA-LLLAKKVA—COOH (SEQ ID NO:2). In a further embodiment the peptide includes the sequence NH$_2$-AMLIMTML-LAKKVA-COOH (SEQ ID NO:3).

The BID α6 peptides can be polymers of L-amino acids, D-amino acids, or a combination of both. For example, in various embodiments, the peptides are D retro-inverso peptides. The term "retro-inverso isomer" refers to an isomer of a linear peptide in which the direction of the sequence is reversed and the chirality of each amino acid residue is inverted. See, e.g., Jameson et al., *Nature,* 368, 744-746 (1994); Brady et al., *Nature*, 368, 692-693 (1994). The net result of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence of the invention may be made into an D retro-inverso peptide by synthesizing a reverse of the sequence for the corresponding native L-amino acid sequence.

BID Mutein

In another aspect, the invention provides a BID mutein. A BID mutein polypeptide includes a polypeptide where one or more of amino acid residues in a wt BID polypeptide are mutated. These mutations result in a BID α6 mutein displaying decreased triggering of cytochrome c release from the mitochondria compared to wt BID. In various other embodiments the BID mutein does not dimerize with BAX, BCL-2 or BCL-$X_L$. In a further embodiment, the BID mutein peptide inhibits apoptosis.

The term "mutein" as used herein refers to a variant form of wt BID that displays decreased triggering of cytochrome c release compared to the wt BID.

Exemplary wt BID proteins include for example the native full-length human BID polypeptide (GenBank Accession No.: NM_001196); rat BID (GenBank Accession No.: NM_022684) and murine BID (GenBank Accession No.: NM_007544). The sequences of these polypeptides are provide below:

Human BID (SEQ ID NO: 4)
MDCEVNNGSSLRDECITNLLVFGFLQSCSDNSFRRELDALGHELPVLAPQ

WEGYDELQTDGNRSSHSRLGRIEADSESQEDIIRNIARHLAQVGDSMDRS

IPPGLVNGLALQLRNTSRSEEDRNRDLATALEQLLQAYPRDMEKEKTMLV

LALLLAKKVASHTPSLLRDVFHTTVNFINQNLRTYVRSLARNGMD.

Rat BID (SEQ ID NO: 5)
MDSEVSNGSGLGAEHITNLLVFGFLRNNDRDFHQELEVLGQELPVQVYLE

GDREDELQTDGSRASRSFYHGRIEPDSESQDEVIHNIARHLAQAGDELDH

SIQPTLVRQLAAQFMNGSLSEEDKRNCLAKALDEVKTSFPRDMENDKAML

IMTMLLAKKVASHAPSLLRDVFRTTVNFINQNLFSYVRDLVRNEMD.

Murine BID (SEQ ID NO: 6)
MDSEVSNGSGLGAKHITDLLVFGFLQSSGCTRQELEVLGRELPVQAYWEA

DLEDELQTDGSQASRSFNQGRIEPDSESQEEIIHNIARHLAQIGDEMDHN

IQPTLVRQLAAQFMNGSLSEEDKRNCLAKALDEVKTAFPRDMENDKAMLI

MTMLLAKKVASHAPSLLRDVFHTTVNFINQNLFSYVRNLVRNEMD.

A BID mutein, includes a polypeptide where the amino acid at position 157, when numbered in accordance with murine wt BID, is not a lysine. Alternatively, a BID mutein includes a polypeptide where the amino acid at position 158 is not a lysine. Preferably, a BID mutein includes a polypeptide where the amino acids at position 157 and 158 are not lysine residues. Preferably, the amino acids at positions 157 and/or 158 are alanine residues.

No particular length is implied by the term "mutein polypeptide". In some embodiments, the mutein is less than 195 amino acids in length, e.g., less than or equal to 150, 100, 75, 50, 35, 25 or 15 amino acid in length. In various embodiments, the mutein includes the amino acid sequence of SEQ ID NO: 7-9 where the mutein displays decreased triggering of cytochrome c release compared to the wt BID. In another embodiment, the mutein peptide does not dimerize with BAX, BCL-2 or BCL-$X_L$. In a further embodiment, the BID mutein peptide inhibits apoptosis.

Examples of BID mutein peptides include a polypeptide which includes (in whole or in part) the sequence NH$_2$-XM-LXXXXLLAAAVA-COOH (SEQ ID NO:7). As used herein X may be any amino acid. In another embodiment, the peptide includes the sequence NH$_2$-AMLIMTMLLAAAVA-COOH (SEQ ID NO:8). In a further embodiment, the peptide includes the sequence NH$_2$-TMLVLALLLAAAVA-COOH (SEQ ID NO:9).

The invention also includes a mutant or variant protein any of whose residues may be changed from wt BID while still encoding a protein that maintains BID mutein activities (i.e. displaying decreased triggering of cytochrome c release from the mitochondria compared to wt BID) and physiological functions, or a functional fragment thereof. In some embodiments, up to 20% or more of the residues may be so changed in the mutant or variant protein. Preferably, the BID mutein is at least about 80% homologous to wt BID, more preferably at least about 85%, 90%, 95%, 98%, and most preferably at least about 99% homologous to wt BID. In general, a BID-like variant that preserves BID mutein-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined. BID mutein-like activities includes, for example, decreased mitochondrial inner membrane remodeling, decreased cytochrome c mobilization, does not dimerize with BAX, BCL-2 or BCL-$X_L$, or inhibits apoptosis.

Minor modifications of the wt BID primary amino acid sequence may result in proteins which function to affect mitochondrial inner membrane remodeling and cytochrome c mobilization and have substantially equivalent activity as compared to the BID mutein polypeptide described herein. These minor modifications include the minor differences found in the sequence of wt BID polypeptide isolated from different species (e.g., human, mouse, and rat BID). Such proteins include those as defined by the term "having essentially the amino acid sequence" of the wt BID or BID mutein of the invention. Such modifications may be deliberate, as by site-directed mutagenesis, or may be spontaneous, as those found in different species. All of the polypeptides produced by these modifications are included herein as long as the biological activity of mutein BID still exists, and the polypeptide is capable of decreasing mitochondrial inner membrane remodeling and cytochrome c mobilization as compared to wt BID. Further, deletions of one or more amino acids can also result in modification of the structure of the resultant molecule without significantly altering its biological activity.

Preparation of BID α6 Peptide and BID Mutein Polypeptides

BID α6 peptides and BID mutein polypeptides are easily prepared using modern cloning techniques, or may be synthesized by solid state methods by site-directed mutagenesis. A BID α6 peptide and BID mutein polypeptide may include dominant negative forms of a polypeptide. In one embodiment, native BID α6 peptides and BID mutein polypeptides can be isolated from cells or tissue sources by an appropriate purification scheme using standard protein purification techniques. In another embodiment, BID α6 peptides or BID mutein polypeptides are produced by recombinant DNA techniques. Alternative to recombinant expression, BID α6 peptides or BID mutein polypeptides can be synthesized chemically using standard peptide synthesis techniques.

An "isolated" or "purified" protein or biologically active portion thereof is substantially free of cellular material or other contaminating proteins from the cell or tissue source from which the BID α6 peptide and BID mutein polypeptide is derived, or substantially free from chemical precursors or other chemicals when chemically synthesized. The language "substantially free of cellular material" includes preparations of BID α6 peptides and BID mutein polypeptides in which the protein is separated from cellular components of the cells from which it is isolated or recombinantly produced. In one embodiment, the language "substantially free of cellular material" includes preparations of BID α6 peptides and BID mutein polypeptides having less than about 30% (by dry weight) of non-BID α6 peptide and BID mutein polypeptide (also referred to herein as a "contaminating protein"), more preferably less than about 20% of non-BID α6 peptide and BID mutein polypeptide, still more preferably less than about 10% of non-BID α6 peptide and BID mutein polypeptide, and most preferably less than about 5% non-BID α6 peptide and BID mutein polypeptide. When the BID α6 peptide and BID mutein polypeptide or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of BID α6 peptides and BID mutein polypeptides in which the protein is separated from chemical precursors or other chemicals that are involved in the synthesis of the protein. In one embodiment, the language "substantially free of chemical precursors or other chemicals" includes preparations of BID α6 peptides and BID mutein polypeptide having less than about 30% (by dry weight) of chemical precursors or non-BID α6 peptide and BID mutein polypeptide chemicals, more preferably less than about 20% chemical precursors or non-BID α6 peptide and BID mutein polypeptide chemicals, still more preferably less than about 10% chemical precursors or non-BID α6 peptide and BID mutein polypeptide chemicals, and most preferably less than about 5% chemical precursors or non-BID α6 peptide and BID mutein polypeptide chemicals.

The term "biologically equivalent" is intended to mean that the compositions of the present invention are capable of demonstrating some or all of the same apoptosis modulating effects although not necessarily to the same degree as the BID or BID α6 polypeptide deduced from sequences identified from cDNA libraries of human, rat or mouse origin or produced from recombinant expression symptoms.

By "substantially homologous" it is meant that the degree of homology of human, rat and mouse BID α6 peptides and BID mutein polypeptides to a BID α6 peptide and BID mutein polypeptide from any species is greater than that between BID α6 peptides and BID mutein polypeptides and any previously reported member of the BCL-2 family of proteins.

Percent conservation is calculated from the above alignment by adding the percentage of identical residues to the percentage of positions at which the two residues represent a conservative substitution (defined as having a log odds value of greater than or equal to 0.3 in the PAM250 residue weight table). Conservation is referenced to sequences as indicated above for identity comparisons. Conservative amino acid changes satisfying this requirement are: R-K; E-D, Y-F, L-M; V-I, Q-H.

BID α6 peptides and BID mutein polypeptides can also include derivatives of BID α6 peptides and BID mutein polypeptides which are intended to include hybrid and modified forms of BID α6 peptides and BID mutein polypeptide including fusion proteins and BID α6 peptide and BID mutein polypeptide fragments and hybrid and modified forms in which certain amino acids have been deleted or replaced and modifications such as where one or more amino acids have been changed to a modified amino acid or unusual amino acid and modifications such as glycosylation so long as the hybrid or modified form retains the biological activity of BID α6 peptides and BID mutein polypeptides. By retaining the biological activity, it is meant that cell death is induced by the BID or BID α6 polypeptide, although not necessarily at the same level of potency as that of the naturally-occurring BID or BID α6 polypeptide identified for human or mouse and that can be produced, for example, recombinantly. The terms induced and stimulated are used interchangeably throughout the specification. Alternatively, by retaining the biological activity, it is meant that cell death is prevented by the BID α6 mutein polypeptide when compared to the cell death inducible ability of the naturally-occurring BID or BID α6 polypeptide identified for human or mouse and that can be produced, for example, recombinantly. The terms prevented and inhibited are used interchangeably throughout the specification.

Preferred variants are those that have conservative amino acid substitutions made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a BID or BID α6 polypeptide is replaced with another amino acid residue from the same side chain family. Alternatively, in another embodiment, mutations can be introduced randomly along all or part of a BID or BID α6 coding sequence, such as by saturation mutagenesis, and the resultant mutants can be screened to identify mutants that retain activity.

Also included within the meaning of substantially homologous is any BID α6 peptide and BID mutein polypeptide which may be isolated by virtue of cross-reactivity with antibodies to the BID α6 peptide and BID mutein polypeptide described herein or whose encoding nucleotide sequences including genomic DNA, mRNA or cDNA may be isolated through hybridization with the complementary sequence of genomic or subgenomic nucleotide sequences or cDNA of the BID α6 and BID mutein polynucleotides herein or fragments thereof. It will also be appreciated by one skilled in the art that degenerate DNA sequences can encode human BID α6 and BID mutein polynucleotide sequences and these are also intended to be included within the present invention as are allelic variants of BID α6 and BID mutein.

BID α6 or BID Mutein Chimeric and Fusion Proteins

The invention also provides BID α6 and BID mutein chimeric or fusion proteins. As used herein, a BID α6 or BID mutein "chimeric protein" or "fusion protein" comprises a BID α6 or BID mutein polypeptide operatively linked to a non-BID α6 or BID mutein polypeptide. An "BID α6 or BID mutein polypeptide" refers to a polypeptide having an amino acid sequence corresponding to a BID α6 peptide or BID mutein polypeptide, whereas a "non-BID α6 peptide or BID mutein polypeptide" refers to a polypeptide having an amino acid sequence corresponding to a protein that is not substantially homologous to the BID α6 peptide or BID mutein polypeptide, e.g., a protein that is different from the BID α6 peptide or BID mutein polypeptide and that is derived from the same or a different organism. Within a BID α6 peptide and BID mutein fusion protein the BID α6 peptide and BID mutein polypeptide can correspond to all or a portion of a BID α6 peptide and BID mutein polypeptide. In one embodiment, a BID α6 peptide and BID mutein fusion protein comprises at least one biologically active portion of a BID α6 peptide and BID mutein polypeptide. In another embodiment, a BID α6 peptide and BID mutein fusion protein comprises at least two biologically active portions of a BID α6 peptide and BID mutein polypeptide. Within the fusion protein, the term "operatively linked" is intended to indicate that the BID α6 peptide and BID mutein polypeptide and the non-BID α6 peptide and BID mutein polypeptide are fused in-frame to each other. The non-BID α6 peptide and BID mutein polypeptide can be fused to the N-terminus or C-terminus of the BID α6 peptide and BID mutein polypeptide.

For example, in one embodiment a BID α6 peptide and BID mutein fusion protein comprises a BID α6 peptide and BID mutein polypeptide operably linked to the extracellular domain of a second protein. Such fusion proteins can be further utilized in screening assays for compounds that modulate BID α6 peptide and BID mutein polypeptide activity (such assays are described in detail below).

In another embodiment, the fusion protein is a GST-BID α6 peptide and BID mutein fusion protein in which the BID α6 peptide and BID mutein polypeptide sequences are fused to the C-terminus of the GST (i.e., glutathione S-transferase) sequences. Such fusion proteins can facilitate the purification of recombinant BID α6 peptide and BID mutein polypeptide.

In another embodiment, the fusion protein is a BID α6 peptide and BID mutein polypeptide-immunoglobulin fusion protein in which the BID α6 peptide and BID mutein polypeptide sequences comprising one or more domains are fused to sequences derived from a member of the immunoglobulin protein family. The BID α6 peptide and BID mutein polypeptide-immunoglobulin fusion proteins of the invention can be incorporated into pharmaceutical compositions and administered to a subject to inhibit an interaction between a BID α6 peptide and BID mutein polypeptide ligand and a BID α6 peptide and BID mutein polypeptide on the surface of a cell, to thereby suppress BID α6 peptide and BID mutein polypeptide-mediated signal transduction in vivo. In one non-limiting example, a contemplated BID α6 peptide and BID mutein polypeptide ligand of the invention is a VHL polypeptide. The BID α6 peptide and BID mutein polypeptide-immunoglobulin fusion proteins can be used to affect the bioavailability of a BID α6 peptide and BID mutein polypeptide cognate ligand. Inhibition of the BID α6 peptide and BID mutein polypeptide ligand/BID α6 peptide and BID mutein polypeptide interaction may be useful therapeutically for both the treatment of proliferative disorders, as well as modulating (e.g., inducing or inhibiting) cell survival or apoptosis. For example, inhibition of the BID α6 peptide and BID mutein polypeptide ligand/BID α6 peptide and BID mutein polypeptide can be used to various disorders as described herein. Moreover, the BID α6 peptide and BID mutein polypeptide-immunoglobulin fusion proteins of the invention can be used as immunogens to produce anti-BID α6 and BID mutein antibodies in a subject, to purify BID α6 peptide and BID mutein polypeptide ligands, and in screening assays to identify molecules that inhibit the interaction of BID α6 peptide and BID mutein polypeptide with a BID α6 peptide and BID mutein polypeptide ligand.

In another embodiment, the fusion protein is a BID α6 peptide and BID mutein polypeptide-transduction domain fusion protein in which the BID α6 peptide and BID mutein polypeptide sequences comprising one or more domains are fused to a protein transduction domain. The BID α6 peptide and BID mutein polypeptide-transduction domain fusion proteins of the invention can be incorporated into pharmaceutical compositions and administered to a subject to inhibit an interaction between a BID α6 peptide and BID mutein polypeptide ligand and a BID α6 peptide and BID mutein polypeptide in a cell, to thereby suppress BID α6 peptide and BID mutein polypeptide-mediated signal transduction in vivo. Several examples of biologically active fusion proteins, comprising transduction domains, for direct delivery of proteins into human patients in the context of protein therapy are known in the art, including, but not limited to, the human immunodeficiency virus type 1 (HIV-1) TAT protein. These transducing proteins have been shown to be able to carry large biomolecules from the extracellular environment directly into the cytoplasm and nucleus of cells, both in vivo and in vitro. These cells can be mammalian cells (i.e. human cells). These fusion proteins have the ability to increase the delivery of plasmid DNA to the nuclei of cells in vivo and thereby increase gene expression and have been used to address a number of biological questions related to cell cycle progression and apoptosis (Nagahara et al., Nat Med 4: 1449-52, 1998; Gius et al., Cancer Res 59: 2577-80, 1999; Schwarze et al., Science 285: 1569-72, 1999; Schwarze and Dowdy, Trends Pharmacol Sci 21: 45-8, 2000; Ho et al., Cancer Res 61: 474-7, 2001; Vocero-Akbani et al., Methods Enzymol 332: 36-49, 2001; Snyder and Dowdy, Curr Opin Mol Ther 3: 147-52, 2001). Methods of producing and transducing TAT fusion proteins are described (Becker-Hapak et. al., Methods 24: 247-56, 2001).

In another embodiment, the fusion protein is a BID α6 peptide and BID mutein polypeptide-basic charged domain fusion protein in which the BID α6 peptide and BID mutein polypeptide sequences comprising one or more domains are fused to a basic peptide domain. The BID α6 peptide and BID mutein polypeptide-basic charged domain fusion proteins of the invention can be incorporated into pharmaceutical compositions and administered to a subject to inhibit an interaction between a BID α6 peptide and BID mutein polypeptide ligand and a BID α6 peptide and BID mutein polypeptide in a cell, to thereby suppress BID α6 peptide and BID mutein polypeptide-mediated signal transduction in vivo. Several examples of biologically active fusion proteins, comprising basic peptide domains, for direct delivery of proteins into human patients in the context of protein therapy are known in the art, including, but not limited to, the human immunodeficiency virus type 1 (HIV-1) TAT protein, HIV-1 Rev protein, Drosophila Antennapedia or HIV-1 octaarginine protein. These basic peptide domains can be arginine-rich. These transducing proteins have been shown to have a membrane permeability and a carrier function for the delivery of proteins to the cytoplasm and nucleus of cells, both in vivo and in vitro. These cells can be mammalian cells (i.e. human cells) (Suzuki et al., J Biol Chem 276: 5836-40, 2001 and Suzuki et al., J Biol Chem 277: 2437-43, 2002).

A BID α6 and BID mutein chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (Eds.) CURRENT PROTOCOLS IN MOLECULAR BIOLOGY, John Wiley & Sons, 1992). Moreover, many expression vectors are commercially available that already encode a fusion moiety (e.g., a GST polypeptide). A BID α6 peptide and BID mutein polypeptide-encoding nucleic acid can be cloned into such an expression vector such that the fusion moiety is linked in-frame to the BID α6 peptide and BID mutein polypeptide.

BID α6 or BID Mutein Nucleic Acids

The present invention additionally relates to nucleic acids that encode BID α6 and BID mutein nucleic acids. Nucleic acids encoding the BID α6 peptides and BID mutein polypeptides may be obtained by any method known in the art (e.g., by PCR amplification using synthetic primers hybridizable to the 3'- and 5'-termini of the sequence and/or by cloning from a cDNA or genomic library using an oligonucleotide sequence specific for the given gene sequence).

For recombinant expression of one or more BID α6 peptides and BID mutein polypeptides, the nucleic acid containing all or a portion of the nucleotide sequence encoding the peptide may be inserted into an appropriate expression vector (i.e., a vector that contains the necessary elements for the transcription and translation of the inserted peptide coding sequence). In some embodiments, the regulatory elements are heterologous (i.e., not the native gene promoter). Alternately, the necessary transcriptional and translational signals may also be supplied by the native promoter for the genes and/or their flanking regions.

A variety of host-vector systems may be utilized to express the peptide coding sequence(s). These include, but are not limited to: (i) mammalian cell systems that are infected with vaccinia virus, adenovirus, and the like; (ii) insect cell systems infected with baculovirus and the like; (iii) yeast containing yeast vectors or (iv) bacteria transformed with bacteriophage, DNA, plasmid DNA, or cosmid DNA. Depending upon the host-vector system utilized, any one of a number of suitable transcription and translation elements may be used.

Promoter/enhancer sequences within expression vectors may utilize plant, animal, insect, or fungus regulatory sequences, as provided in the invention. For example, promoter/enhancer elements can be used from yeast and other fungi (e.g., the GAL4 promoter, the alcohol dehydrogenase promoter, the phosphoglycerol kinase promoter, the alkaline phosphatase promoter). Alternatively, or in addition, they may include animal transcriptional control regions, e.g., (i) the insulin gene control region active within pancreatic β-cells (see, e.g., Hanahan, et al., 1985. Nature 315: 115-122); (ii) the immunoglobulin gene control region active within lymphoid cells (see, e.g., Grosschedl, et al., 1984. Cell 38: 647-658); (iii) the albumin gene control region active within liver (see, e.g., Pinckert, et al., 1987. Genes and Dev 1: 268-276; (iv) the myelin basic protein gene control region active within brain oligodendrocyte cells (see, e.g., Readhead, et al., 1987. Cell 48: 703-712); and (v) the gonadotropin-releasing hormone gene control region active within the hypothalamus (see, e.g., Mason, et al., 1986. Science 234: 1372-1378), and the like.

Expression vectors or their derivatives include, e.g. human or animal viruses (e.g., vaccinia virus or adenovirus); insect viruses (e.g., baculovirus); yeast vectors; bacteriophage vectors (e.g., lambda phage); plasmid vectors and cosmid vectors.

A host cell strain may be selected that modulates the expression of inserted sequences of interest, or modifies or processes expressed peptides encoded by the sequences in the specific manner desired. In addition, expression from certain promoters may be enhanced in the presence of certain inducers in a selected host strain; thus facilitating control of the expression of a genetically-engineered peptides. Moreover, different host cells possess characteristic and specific mechanisms for the translational and post-translational processing and modification (e.g., glycosylation, phosphorylation, and the like) of expressed peptides. Appropriate cell lines or host systems may thus be chosen to ensure the desired modification and processing of the foreign peptide is achieved. For example, peptide expression within a bacterial system can be used to produce an unglycosylated core peptide; whereas expression within mammalian cells ensures "native" glycosylation of a heterologous peptide.

Also included in the invention are derivatives, fragments, homologs, analogs and variants of BID α6 peptides and BID mutein polypeptides and nucleic acids encoding these peptides. For nucleic acids, derivatives, fragments, and analogs provided herein are defined as sequences of at least 6 (contiguous) nucleic acids, and which have a length sufficient to allow for specific hybridization. For amino acids, derivatives, fragments, and analogs provided herein are defined as sequences of at least 4 (contiguous) amino acids, a length sufficient to allow for specific recognition of an epitope.

The length of the fragments is less than the length of the corresponding full-length nucleic acid or polypeptide from which the BID α6 peptides and BID mutein polypeptides, or nucleic acid encoding same, is derived. Derivatives and analogs may be full length or other than full length, if the derivative or analog contains a modified nucleic acid or amino acid. Derivatives or analogs of the BID α6 peptides and BID mutein polypeptides include, e.g., molecules including regions that are substantially homologous to the peptides, in various embodiments, by at least about 30%, 50%, 70%, 80%, or 95%, 98%, or even 99%, identity over an amino acid sequence of identical size or when compared to an aligned sequence in which the alignment is done by a computer homology program known in the art. For example sequence identity can be measured using sequence analysis software (Sequence Analysis Software Package of the Genetics Computer Group, University of Wisconsin Biotechnology Center, 1710 University Avenue, Madison, Wis. 53705), with the default parameters therein.

In the case of polypeptide sequences, which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine. Thus, included in the invention are peptides having mutated sequences such that they remain homologous, e.g. in sequence, in function, and in antigenic character or other function, with a protein having the corresponding parent sequence. Such mutations can, for example, be mutations involving conservative amino acid changes, e.g., changes between amino acids of broadly similar molecular properties. For example, interchanges within the aliphatic group alanine, valine, leucine and isoleucine can be considered as conservative. Sometimes substitution of glycine for one of these can also be considered conservative. Other conservative interchanges include those within the aliphatic group aspartate and glutamate; within the amide group asparagine and glutamine; within the hydroxyl group serine and threonine; within the aromatic group phenylalanine, tyrosine and tryptophan; within the basic group lysine, arginine and histidine; and within the sulfur-containing group methionine and cysteine. Sometimes substitution within the group methionine and leucine can also be considered conservative. Preferred conservative substitution groups are aspartate-glutamate; asparagine-glutamine; valine-leucine-isoleucine; alanine-valine; phenylalanine-tyrosine; and lysine-arginine.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide, which is 50% identical to the reference polypeptide over its entire length. Of course, other polypeptides will meet the same criteria.

The invention also encompasses allelic variants of the disclosed polynucleotides or peptides; that is, naturally-occurring alternative forms of the isolated polynucleotide that also encode peptides that are identical, homologous or related to that encoded by the polynucleotides. Alternatively, non-naturally occurring variants may be produced by mutagenesis techniques or by direct synthesis.

Species homologs of the disclosed polynucleotides and peptides are also provided by the present invention. "Variant" refers to a polynucleotide or polypeptide differing from the polynucleotide or polypeptide of the present invention, but retaining essential properties thereof. Generally, variants are overall closely similar, and in many regions, identical to the polynucleotide or polypeptide of the present invention. The variants may contain alterations in the coding regions, non-coding regions, or both.

In some embodiments, altered sequences include insertions such that the overall amino acid sequence is lengthened while the protein retains trafficking properties. Additionally, altered sequences may include random or designed internal deletions that shorten the overall amino acid sequence while the protein retains transport properties.

The altered sequences can additionally or alternatively be encoded by polynucleotides that hybridize under stringent conditions with the appropriate strand of the naturally-occurring polynucleotide encoding a polypeptide or peptide from which the BID α6 peptide and BID mutein polypeptide is derived. The variant peptide can be tested for BID α6 peptide and BID mutein polypeptide-binding and modulation of BID α6 peptide and BID mutein polypeptide-mediated activity using the herein described assays. 'Stringent conditions' are sequence dependent and will be different in different circumstances. Generally, stringent conditions can be selected to be about 5° C. lower than the thermal melting point ($T_M$) for the specific sequence at a defined ionic strength and pH. The $T_M$ is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may affect the stringency of hybridization (including, among others, base composition and size of the complementary strands), the presence of organic solvents and the extent of base mismatching, the combination of parameters is more important than the absolute measure of any one.

High stringency can include, e.g., Step 1: Filters containing DNA are pretreated for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Step 2: Filters are hybridized for 48 hours at 65° C. in the above prehybridization mixture to which is added 100 mg/ml denatured salmon sperm DNA and 5-20×10$^6$ cpm of $^{32}$P-labeled probe. Step 3: Filters are washed for 1 hour at 37° C. in a solution containing 2×SSC, 0.01% PVP, 0.01% Ficoll, and 0.01% BSA. This is followed by a wash in 0.1×SSC at 50° C. for 45 minutes. Step 4: Filters are autoradiographed. Other conditions of high stringency that may be used are well known in the art. See, e.g., Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

Moderate stringency conditions can include the following: Step 1: Filters containing DNA are pretreated for 6 hours at 55° C. in a solution containing 6×SSC, 5× Denhardt's solution, 0.5% SDS and 100 mg/ml denatured salmon sperm DNA. Step 2: Filters are hybridized for 18-20 hours at 55° C. in the same solution with 5-20×106 cpm $^{32}$P-labeled probe added. Step 3: Filters are washed at 37° C. for 1 hour in a solution containing 2×SSC, 0.1% SDS, then washed twice for 30 minutes at 60° C. in a solution containing 1×SSC and 0.1% SDS. Step 4: Filters are blotted dry and exposed for autoradiography. Other conditions of moderate stringency that may be used are well-known in the art. See, e.g., Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

Low stringency can include: Step 1: Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Step 2: Filters are hybridized for 18-20 hours at 40° C. in the same solution with the addition of 0.02% PVP, 0.02% Ficoll, 0.2% BSA, 100 µg/ml salmon sperm DNA, 10% (wt/vol) dextran sulfate, and 5-20× 106 cpm $^{32}$P-labeled probe. Step 3: Filters are washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Step 4: Filters are blotted dry and exposed for autoradiography. If necessary, filters are washed for a third time at 65-68° C. and reexposed to film. Other conditions of low stringency that may be used are well known in the art (e.g., as employed for cross-species hybridizations). See, e.g., Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

BID α6 or BID Mutein Antibodies

Also included in the invention are antibodies to BID α6 peptides and BID mutein polypeptides or fragments thereof. The term "antibody" as used herein refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. In general, an antibody molecule obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

An isolated BID α6 and BID mutein-related protein of the invention may be intended to serve as an antigen, or a portion or fragment thereof, and additionally can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein, or amino acid sequences as shown in SEQ ID NOs:1-7, and encompasses an epitope thereof such that an antibody raised against the peptide forms a specific immune complex with the full length protein or with any fragment that contains the epitope. By epitope reference is made to an antigenic determinant of a polypeptide. Typically, epitopes contain hydrophilic amino acids such that the particular region of the polypeptide is located on its surface and likely to be exposed in an aqueous based milieu. Preferably, the antigenic peptide comprises at least 3 amino acid residues in a spatial conformation which is unique to the epitope. Generally, the antigenic peptide comprises at least 5 amino acid residues, or at least 10 amino acid residues, or at least 15 amino acid residues, or at least 20 amino acid residues, or at least 30 amino acid residues. Furthermore, antibodies to a BID α6 peptide and BID mutein polypeptide or fragments thereof can also be raised against oligopeptides that include a conserved region such as the α6 helix domain of BID identified herein.

In certain embodiments of the invention, at least one epitope encompassed by the antigenic peptide is a region of BID α6 and BID mutein-related protein that is located on the surface of the protein, e.g., a hydrophilic region. A hydrophobicity analysis of the human BID α6 and BID mutein-related protein sequence will indicate which regions of a BID α6 and BID mutein-related protein are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, Proc. Nat. Acad. Sci. USA 78: 3824-3828; Kyte and Doolittle 1982, J. Mol. Biol. 157: 105-142, each of which is incorporated herein by reference in its entirety. Antibodies that are specific for one or more domains within an antigenic protein, or derivatives, fragments, analogs or homologs thereof, are also provided herein.

A protein of the invention, or a derivative, fragment, analog, homolog or ortholog thereof, may be utilized as an immunogen in the generation of antibodies that immunospecifically bind these protein components.

Various procedures known within the art may be used for the production of polyclonal or monoclonal antibodies directed against a protein of the invention, or against derivatives, fragments, analogs homologs or orthologs thereof (see, for example, Antibodies: A Laboratory Manual, Harlow E, and Lane D, 1988, Cold Spring Harbor Laboratory Press, Cold Spring Harbor, N.Y., incorporated herein by reference). Some of these antibodies are discussed below.

Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and *Corynebacterium parvum*, or similar immunostimulatory agents. Additional examples of adjuvants which can be employed include MPL-TDM adjuvant (monophosphoryl Lipid A, synthetic trehalose dicorynomycolate) and CpG dinucleotide motifs (Krieg, A. M. Biochim Biophys Acta 1489(1):107-16, 1999).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

Monoclonal Antibodies

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Preferably, antibodies having a high degree of specificity and a high binding affinity for the target antigen are isolated.

After the desired hybridoma cells are identified, the clones can be subcloned by limiting dilution procedures and grown by standard methods. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Humanized Antibodies

The antibodies directed against the protein antigens of the invention can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, Curr. Op. Struct. Biol., 2:593-596 (1992)).

Human Antibodies

Fully human antibodies relate to antibody molecules in which essentially the entire sequences of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized in the practice of the present invention and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries (Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (Bio/Technology 10, 779-783 (1992)); Lonberg et al. (Nature 368 856-859 (1994)); Morrison (Nature 368, 812-13 (1994)); Fishwild et al, (Nature Biotechnology 14, 845-51 (1996)); Neuberger (Nature Biotechnology 14, 826 (1996)); and Lonberg and Huszar (Intern. Rev. Immunol. 13 65-93 (1995)).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example, of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

$F_{ab}$ Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., 1991 *EMBO J.*, 10:3655-3659.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full-length antibodies or antibody fragments (e.g. F(ab')₂ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')₂ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from *E. coli* and chemically coupled to form bispecific antibodies. Shalaby et al., J. Exp. Med. 175:217-225 (1992) describe the production of a fully humanized bispecific antibody F(ab')₂ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein (BID or BID α6).

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Effector Function Engineering

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., J. Exp Med., 176: 1191-1195 (1992) and Shopes, J. Immunol., 148: 2918-2922 (1992). Homodimeric antibodies with enhanced anti-tumor activity can also be prepared using heterobifunctional crosslinkers as described in Wolff et al. Cancer Research, 53: 2560-2565 (1993). Alternatively, an antibody can be engineered that has dual Fc regions and can thereby have enhanced complement lysis and ADCC capabilities. See Stevenson et al., Anti-Cancer Drug Design, 3: 219-230 (1989).

Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaredehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody can be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

Small Molecules and Peptide Mimetics

Small molecules can mimic the effect of an anti-BID or BID α6 antibody by binding to a BID or BID α6 polypeptide or fragment thereof. Such small molecules can be small polypeptides such as analogues or fragments of part or the full sequence of a BCL-2 family member such as BAX or BCL-2 or BCL-$X_L$ or BID muteins having α6 helix domain mutations in which case the polypeptide itself may produce little or no effect on apoptosis, also, the analogue or fragment or mutein in one embodiment is able to bind to a BID or BID α6 polypeptide produced by a cell and thereby diminish the death agonist activity of BID or BID α6. BID or BID α6 polypeptides can also have mutations within the α6 helix domain such that the BID or BID α6 mutein has little or no effect on apoptosis but can prevent the binding of a BID or BID α6 polypeptide produced by a cell to thereby modulate the death agonist activity of BID or BID α6 within the cell.

Non-peptidal substances possessing the biological properties of BID or BID α6 polypeptides in eliciting an apoptotic state or antagonists BID or BID α6 polypeptides or fragments of BID or BID α6 polypeptides can also be made. The techniques for development of peptide mimetics are well known in the art. (See for example, Navia and Peattie, Trends Pharm Sci 14: 189-195, 1993; Olson et al, J Med Chem 36: 3039-3049 which are incorporated by reference). Typically this involves identification and characterization of the protein target site as well as the protein ligand using X-ray crystallography and nuclear magnetic resonance technology. The amino acid sequence of the BID or BID α6 polypeptide and the α6 helix domain which is described herein. Using this information along with computerized molecular modeling, a pharmacophore hypothesis is developed and compounds are made and tested in an assay system.

Methods of Inhibiting Apoptosis

Also included in the invention are methods inhibiting apoptosis. Apoptosis, also known as programmed cell death, plays a role in development, aging and in various pathologic conditions. In developing organisms, both vertebrate and invertebrate, cells die in particular positions at particular times as part of the normal morphogenetic process. The process of apoptosis is characterized by, but not limited to, several events. Cells lose their cell junctions and microvilli, the cytoplasm condenses and nuclear chromatin marginates into a number of discrete masses. As the nucleus fragments, the cytoplasm contracts and mitochondria and ribosomes become densely compacted. After dilation of the endoplasmic reticulum and its fusion with the plasma membrane, the cell breaks up into several membrane-bound vesicles, apoptotic bodies, which are usually phagocytosed by adjacent bodies. As fragmentation of chromatin into oligonucleotides fragments is characteristic of the final stages of apoptosis, DNA cleavage patterns can be used as and in vitro assay for its occurrence (Cory, Nature 367: 317-18, 1994).

In one aspect, the invention provides a method of treating or preventing an apoptosis-associated disorder in a subject in need thereof by administering to the subject a therapeutically effective amount of a BID α6-inhibitor so apoptosis is inhibited. The subject can be e.g., any mammal, e.g., a human, a primate, mouse, rat, dog, cat, cow, horse, pig. The term "therapeutically effective" means that the amount of BID α6-inhibitor, for example, which is used, is of sufficient quantity to ameliorate the apoptosis-associated disorder.

An apoptosis associated disorder includes for example, immunodeficiency diseases, including AIDS/HIV, senescence, neurodegenerative diseases, any degenerative disorder, ischemic and reperfusion cell death, acute ischemic injury, infertility, wound-healing, and the like.

Many methods for measuring apoptosis, including those described herein, are known to the skilled artisan including, but not limited to, the classic methods of DNA ladder formation by gel electrophoresis and of morphologic examination by electron microscopy. The more recent and readily used method for measuring apoptosis is flow cytometry. Flow cytometry permits rapid and quantitative measurements on apoptotic cells. Many different flow cytometric methods for the assessment of apoptosis in cells have been described (Darzynkiewicz et al. Cytometry 13: 795-808, 1992). Most of these methods measure apoptotic changes in cells by staining with various DNA dyes (i.e. propidium iodide (PI), DAPI, Hoechst 33342), however, techniques using the terminal deoxynucleotidyl transferase (TUNNEL) or nick translation assays have also been developed (Gorczyca et al. Cancer Res 53: 1945-1951, 1993). Recently, rapid flow cytometric staining methods that use Annexin V for detection of phosphatidylserine exposure on the cell surface as a marker of apoptosis have become commercially available. The newest flow cytometric assays measure Caspase-3 activity, an early marker of cells undergoing apoptosis and kits for performing this assays are commercially available (Nicholson et al. Nature 376: 37-43, 1995).

A BID α6 inhibitor can be administered with a caspase inhibitor. The caspase inhibitor can be, e.g., a peptide fragment of human cytochrome b, human Tat binding protein, human mitochondrial loop attachment site, a glutamate-binding subunit of a human NMDA receptor complex, human myelin basic protein, human synaptophysin p38, human snRNP protein B, human protein 1, human ubiquitin C-terminal hydrolase, human tissue inhibitor of metalloprotease-3, human MHC HLA-DRw12-MHC class II beta chain, human transglutaminase, human death associated protein 1, human hnRNP D, viral protein p35, synthetic peptides z-VAD-fmk, IETD/fmk, CrmA, AC-DEVD-fmk, YVAD-cmk or z-DEVD-fmk.

In another aspect apoptosis is inhibited in a cell by contacting a cell with a BID α6 inhibitor in an amount sufficient to inhibit apoptosis. The cell population that is exposed to, i.e., contacted with, the BID α6 inhibitor can be any number of cells, i.e., one or more cells, and can be provided in vitro, in vivo, or ex vivo.

A BID α6 inhibitor can prevent apoptosis by inhibiting cytochrome c release from mitochondrial cristae. A BID α6 inhibitor is, for example, (i) a compound which modulates cyclophilin D (e.g., cyclosporin, or cyclosporin A); (ii) a G protein inhibitor (e.g., suramin); (iii) an antibody or antibody fragment that immunospecifically binds to a BID α6 peptide or fragment thereof; (iv) a BID mutein polypeptide or nucleic acid of the invention (e.g., SEQ ID NOs: 7-9).

Methods of Inducing Apoptosis

Also included in the invention are methods of inducing apoptosis. In one aspect apoptosis is induced in subject in need thereof by administering a BID α6 stimulator in an amount sufficient to induce apoptosis. The subject can be e.g., any mammal, e.g., a human, a primate, mouse, rat, dog, cat, cow, horse, pig. In various aspects the subject is susceptible to cancer or an autoimmune disorder.

A BID α6 stimulator can be administered with an anti-angiogenic compound. Examples of an anti-angiogenic compound include, but are not limited to, a tyrosine kinase inhibitor, an epidermal-derived growth factor inhibitor, a fibroblast-derived growth factor inhibitor, a platelet-derived growth factor inhibitor, a matrix metalloprotease (MMP) inhibitor, an integrin blocker, interferon alpha, interferon-inducible protein 10, interleukin-12, pentosan polysulfate, a cyclooxygenase inhibitor, a nonsteroidal anti-inflammatory (NSAID), a cyclooxygenase-2 inhibitor, carboxyamidotriazole, tetrahydrocortisol, combretastatin A-4, squalamine, 6-O-chloro-acetyl-carbonyl)-fumagillol, thalidomide, angiostatin, endostatin, troponin-1, an antibody to VEGF, platelet factor 4 or thrombospondin.

The BID α6 stimulator can further be administered with an chemotherapeutic compound. Examples of chemotherapeutic compounds include, but are not limited to, paclitaxel, Taxol, lovastatin, minosine, tamoxifen, gemcitabine, 5-fluorouracil (5-FU), methotrexate (MTX), docetaxel, vincristine, vinblastin, nocodazole, teniposide, etoposide, adriamycin, epothilone, navelbine, camptothecin, daunonibicin, dactinomycin, mitoxantrone, amsacrine, epirubicin or idarubicin.

In another aspect, apoptosis is induced in a cell by contacting a cell with a BID α6 stimulator in an amount sufficient to induce apoptosis. The cell population that is exposed to, i.e., contacted with, the BID α6 stimulator can be any number of cells, i.e., one or more cells, and can be provided in vitro, in vivo, or ex vivo.

A BID α6 stimulator include for example: (i) any one or more of the BID α6 peptides, and derivative, fragments, analogs and homologs thereof (e.g., SEQ ID NOs: 1-3); (ii) antibodies or antibody fragments directed against the BID α6 peptides; (iii) nucleic acids encoding a BID α6 peptide, and derivatives, fragments, analogs and homologs thereof; (iv) antisense nucleic acids to sequences encoding a BID α6peptide, and (v) modulators (i.e., inhibitors, mimetics, agonists and antagonists).

Some disease conditions are related to the development of a defective down-regulation of apoptosis in the affected cells. For example, neoplasias result, at least in part, from an apoptosis-resistant state in which cell proliferation signals inappropriately exceed cell death signals. Furthermore, some DNA viruses such as Epstein-Barr virus, African swine fever virus and adenovirus, parasitize the host cellular machinery to drive their own replication. At the same time, they modulate apoptosis to repress cell death and allow the target cell to reproduce the virus. Moreover, certain disease conditions such as lymphoproliferative conditions, cancer including drug resistant cancer, arthritis, inflammation, autoimmune diseases and the like may result from a down regulation of cell death regulation. In such disease conditions, it would be desirable to promote apoptotic mechanisms.

Methods of Screening for BID or BID α6 Modulators

The invention further provides a method of screening for BID or BIDα6 modulators, i.e., inhibitors or stimulators.

In various methods, a BID or BIDα6 modulator is identified by contacting a cell with a candidate compound, measuring apoptosis and comparing the amount of apoptosis in the test cell population to a control cell population that has or has not been exposed to the compound A decrease in apoptosis in the presence of the compound as compared to the absence of the compound indicates the compound is an inhibitor of apoptosis. Alternatively an increase in apoptosis in the presence of the compound as compared to the absence of the compound indicates the compound is a stimulator of apoptosis.

The invention also includes an apoptosis modulator (i.e., inhibitor or stimulator) identified according to this screening method, and a pharmaceutical composition which includes the apoptosis modulator.

Methods for Identifying BID Associated Proteins

The invention also provides methods of identifying a BID associated protein by providing a cellular component, contacting the cellular component with an immobilized BID protein, collecting a BID associated cellular component, thereby identifying a BID associated protein. An immobilized BID protein can be a p7/p15 caspase 8 cleaved BID or tBID, including an N-myristoylation p15 fragment (Zha et al., Science, 2000). The BID associated protein can be identified by Western blot analysis or Mass spectrometry.

The invention also includes a BID associated protein identified according to this screening method, and a pharmaceutical composition which includes the BID associated protein.

Pharmaceutical Compositions

The compounds, e.g., BID α6 peptides and BID mutein polypeptides, nucleic acids encoding BID α6 peptides and BID mutein polypeptides, and BID α6 and BID mutein antibodies (also referred to herein as "active compounds") of the invention, and derivatives, fragments, analogs and homologs thereof, can be incorporated into pharmaceutical compositions suitable for administration. Such compositions typically comprise the nucleic acid molecule, or protein, and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a BID α6 peptide and BID mutein polypeptide or BID α6 peptide and BID mutein polypeptide encoding nucleic acid) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, incorporated fully herein by reference.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

The pharmaceutical compositions can be included in a container, pack, or dispenser together with instructions for administration.

The invention will be further described in the following examples, which do not limit the scope of the invention described in the claims.

Example 1

Determination of the Effect of tBID on Cytochrome c Release

Mitochondria were isolated from liver of Balb/cJ mice by standard differential centrifugation, and resuspended in isolation buffer (IB) (0.2 M sucrose, 10 mM Tris-MOPS pH 7.4, 0.1 mM EGTA-Tris, 0.1% delipidated BSA).

To determine the kinetics and extent of tBID induced release of cytochrome c release, mitochondria (0.5 mg/ml) were incubated in experimental buffer (EB) (125 mM KCl, 10 mM Tris-MOPS pH 7.4, 1 mM Pi, 5 mM glutamate, 2.5 mM malate, 10 µM EGTA-Tris, pH 7.4) and treated as described at 25° C. At the indicated time, mitochondria were pelleted by centrifugation at 12000×g at 4° C. for 3 min, and resuspended in the same volume of EB. Cytochrome c release was determined either by densitometry (Stratagene Eagle Eye II, Bio-Rad) of immunoblots, or by rat/mouse specific ELISA performed on mitochondrial pellet and supernatant diluted 1:20 in PBS containing 0.5% Triton X-100 (R&D systems, MN). Cytochrome c is reported as the percentage of the supernatant over the total (pellet plus supernatant).

FIG. 1 shows tBID induced cytochrome c release and effects on light scattering, mitochondrial membrane potential, and calcein release. Panels 1A and 1B are representative immunoblots of cytochrome c in pellets (p) and supernatants (Sn) of mitochondria treated for 45 min with the indicated concentration of tBID (A) or with 320 pmol tBID×mg protein$^{-1}$ for the indicated time (B). Panel 1C shows the concentration dependence of tBID induced cytochrome c release. Panel 1D shows the time course of cytochrome c release by tBID. In panels C and D, data derived from densitometry of immunoblots represent mean±S.D. of 3 different experiments. Panel 1E shows the effects of tBID on light scattering and membrane potential. 0.5 mg/ml mitochondria were incubated in experimental buffer supplemented with 0.3 µM rhodamine 123 (red trace only). Where indicated (arrows), tBID and 400 pmol CCCP×mg protein$^{-1}$ were added. The drop in Rho 123 fluorescence is caused by the addition of mitochondria. Panel 1F shows the release of matrix-entrapped calcein by tBID. 0.5 mg/ml of calcein-loaded mitochondria were incubated for the indicated time with tBID (closed and open circles). Open circles, mitochondria were pretreated for 2 min with 800 pmol CsA×mg protein$^{-1}$. Squares, no tBID. Data represent mean±S.D. of 5 different experiments.

tBID was generated and purified as described in Wei et al., 2000. Wt BID and G94E p22 BID were cleaved with recombinant caspase 8 into the active p7/p15 BID as described (Wei et al., 2000). tBID and p7/p15 BID were dialyzed against 10 mM HEPES (pH 7.6), 1 mM DTT and 125 mM KCl. Unless noted, tBID was used at a final concentration of 320 pmol×mg mitochondrial protein$^{-1}$, whereas p7/p15 BID was used at 3.2 pmol×mg protein$^{-1}$.

Figure 1B:
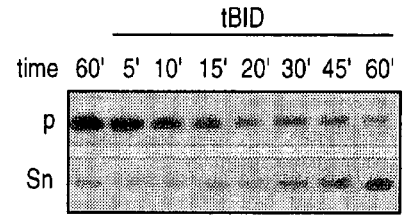
Figure 1C:
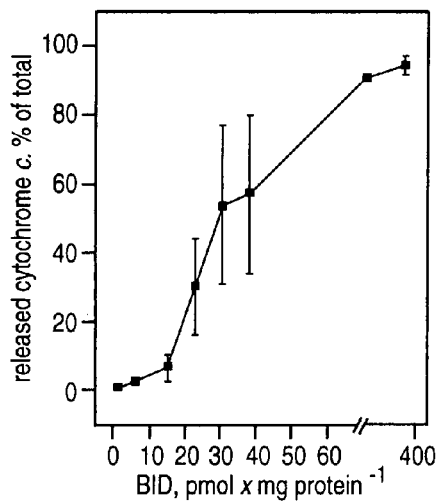
Figure 1D:
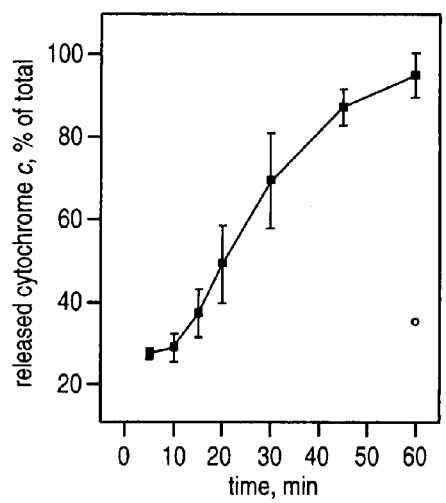
Figure 1E:
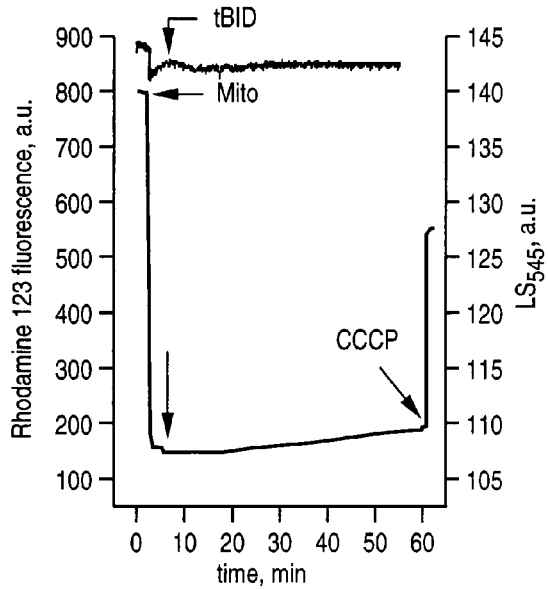

Recombinant tBID displayed a dose dependent release of cytochrome c from mitochondria reaching a plateau at higher tBID concentrations after 45 mins (FIGS. 1A, C). At the concentration of 320 pmol tBID per 1.0 mg of mitochondrial protein, tBID integration into mitochondrial membranes maximized after 15 min, while at lower concentrations it was complete only after 45 mins. Cytochrome c release increased in a time-dependent manner at the maximum tBID concentration (FIGS. 1B, D). Complete cytochrome c release was also observed with 0.32 pmol×mg protein$^{-1}$ of myristoylated p7/p15 BID complex (due to its enhanced mitochondrial targeting). This demonstrated that tBID releases almost all the mitochondrial cytochrome c in a concentration and time dependent manner.

For SDS-PAGE, 20 µg of mitochondrial protein was loaded in each lane of a 12% NuPAGE (NoVex, CA) gel. After separation, proteins were transferred onto PVDF membranes (Immobilon-P, Millipore, Calif.) and membranes were probed as indicated with the following primary antibodies: anti-cytochrome c (Pharmingen, CA, 1:1000); anti-BID (1:1500); anti-BAK (Calbiochem, CA, 1:1000). HRPO-conjugated secondary antibodies (CalTag, CA, 1:2000) were visualized by chemiluminescence (Amersham, N.J.).

Mitochondria were incubated with increasing amounts of digitonin to assess how much cytochrome c was released from IMS by the selective solubilization of the OM (Hoppel and Cooper, 107, 367-375, 1968). To monitor interaction of digitonin with the 1M, uncoupled respiration in the presence of excess exogenous cytochrome c was assessed. Specifically 0.5 mg/ml mitochondria was incubated in EB with the indicated concentration of digitonin. After 5 minutes, mitochondria were centrifuged and cytochrome c content in the resulting pellet and supernatant were determined as described. Uncoupled $J_{O_2}$, uncoupled respiratory rate was recorded in parallel experiments. After 5 minutes of incubation with the indicated concentration of digitonin, mitochondria were treated with 400 pmol CCCP×mg protein-1 in the presence of 10 nmol cytochrome c×mg protein. Approximately 16% of the total cytochrome c could be released by digitonin without substantial respiratory inhibition (no interference of digitonin with the IM) (Table 1), a percentage in agreement with the pool of cytochrome c estimated to reside in the IMS (Bernardi and Azzone, 1981). Therefore, tBID must deploy additional events to enable the release of nearly all cytochrome c from the mitochondrion.

TABLE 1

Effects of Digitonin on Cytochrome c Release and Respiration

|  | Digitonin (pmol × mg protein$^{-1}$) | | | |
| --- | --- | --- | --- | --- |
|  | 0 | 48 | 80 | 145 |
| Cytochrome c release (% of total) | 5.2 | 10.7 | 16.4 | 26.6 |
| Uncoupled J$_{O2}$ (nAt × min$^{-1}$ × mg protein$^{-1}$) | 66.9 | 60 | 60 | 46.7 | tBID was evaluated to determine if it causes any swelling or depolarization that might reflect an opening of the PTP. Swelling of 0.5 mg/ml mitochondria incubated in EB was monitored by changes in side scatter at 545±2.5 nm using LS-50B spectrofluorimeter equipped with magnetic stirring at 25° C. Membrane potential changes of 0.5 mg/ml mitochondria incubated in experimental buffer were monitored from the dequenching of a 0.3 μM Rhodamine 123 (Molecular Probes, OR) solution in a LS-50B spectrofluorimeter at 25° C., using excitation and emission wavelengths set at 503±2.5 nm and 525±5 nm, respectively.

tBID did not induce appreciable mitochondrial swelling over 60 mins, while a slight depolarization was recorded (FIG. 1E) consistent with prior observations (Wei et al., 2000; Shimizu and Tsujimoto, 2000; Kluck et al., 1999; von Ahsen et al., J. Cell Biol. 150, 1027-1036, 2000). However, openings of the PTP can also be transient (Petronilli et al., 1999) with no alterations in membrane potential or light scattering (Bernardi et al., 1999) and can be assessed in mitochondrial populations by following the release of a matrix entrapped fluorophore, calcein (Huser et al., 1998).

Figure 1F:
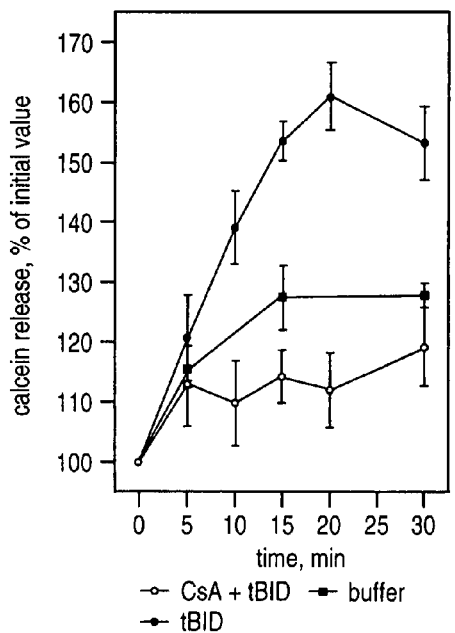

To assess calcein release, mitochondria suspended in IB without BSA were loaded with 10 nmol×mg protein$^{-1}$ calcein-AM (Molecular Probes, Eugene, Oreg.) for 20 mins at room temperature in the dark. Following two washes in IB, the calcein loaded mitochondria were resuspended in IB at a final concentration of 10 mg/ml. 0.5 mg/ml calcein loaded mitochondria were incubated in EB and treated as described. After the indicated time, mitochondria were pelleted. Calcein was measured in an LS-50B spectrofluorimeter (Perkin Elmer) with excitation and emission wavelengths set at 488±2.5 nm and 542±2.5 nm, respectively. Calcein release is reported as the percentage of the calcein measured in the supernatant over the total (pellet plus supernatant). tBID caused a time-dependent increase in the release of matrix calcein and CsA completely inhibits this effect of tBID (FIG. 1F). These results indicate that tBID induces a CsA-sensitive calcein release, but this is not accompanied by any mitochondrial large amplitude swelling that could rupture the OM and account for the complete release of cytochrome c.

Example 2

Determination of the Effects of CsA on Cytochrome c and Adenylate Kinase Release FIG. 2 shows the regulation of tBID induced release of cytochrome c and adenylate kinases versus release of calcein.

Panel 2A shows tBID induction of CsA-insensitive BAK oligomerization. 0.5 mg/ml mitochondria were incubated with tBID (lanes 1-2 and 5-8). In lanes 7-8 mitochondria were pretreated with 800 pmol CsA×mg protein$^{-1}$ for 3 mins. After the indicated time, DMSO (lanes 1-2) or 10 mM BMH (lanes 3-8) was added, and after another 30 min the crosslinking reaction was quenched (Wei et al., 2001). The mitochondria were subjected to SDS-PAGE and immunoblot with anti BAK antibody. Star, BAK multimers.

Panels 2B and 2C show the quantification of the effects of CsA and of blocking anti-BAK antibodies on tBID induced cytochrome c and adenylate kinase (AK) release. In both panels, mitochondria were incubated for the indicated time in the absence (closed squares), or in the presence of tBID (closed circles). Open circles, mitochondria were preincubated for 2 min with 800 pmol CsA×mg protein$^{-1}$, while in open triangles, mitochondria were preincubated for 30 min with 0.1 μg×mg protein$^{-1}$ anti-BAK Ab. Data represent mean±S.D. of 4 different experiments.

Panel 2D shows tBID-induced calcein release in wt and Bak -/- mitochondria. 0.5 mg/ml of calcein loaded wt (squares) or Bak -/- (circles) mitochondria were incubated for the indicated time with tBID (closed symbols). Open symbols, no tBID.

Panel 2E shows the effects of a G94E BID mutant on calcein release. The experiment was performed as in (A), except that wt (closed circles) or G94E (open circles) p7/p15 BID complex was used. Squares, no BID. Triangles, mitochondria were incubated with 800 pmol CsA×mg protein$^{-1}$ for 3 min before the addition of BID.

Figure 2A:
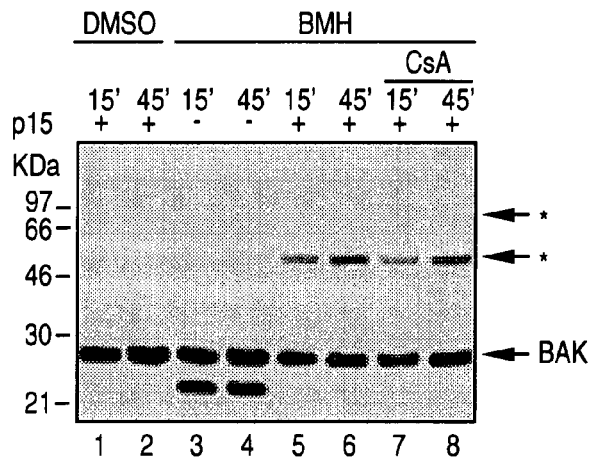
FIG. 2 is a photograph of a Western blot and corresponding line graphs showing regulation of tBID induced release of cytochrome c and adenylate kinases versus release of calcein.
Figure 2B:
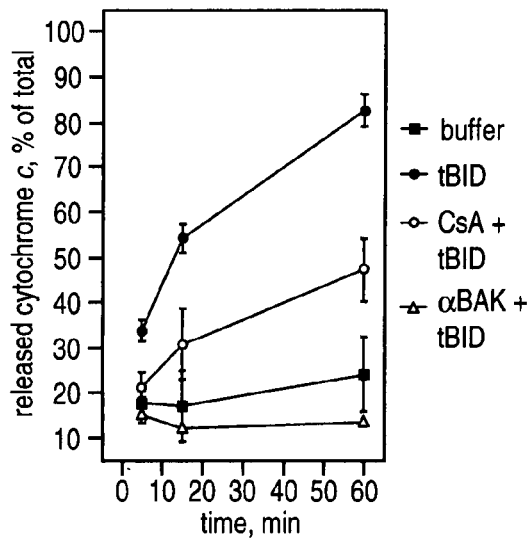

Results show that tBID induces a time-dependent appearance of higher order BAK oligomers that was not affected by CsA (FIG. 2A). Consequently, whether CsA would alter the kinetics or extent of tBID-induced cytochrome c release was assessed. As a control, a blocking anti-BAK antibody did totally prevent cytochrome c release (FIG. 2B). However, CsA only partially interfered with tBID induced release of cytochrome c (FIG. 2B). The release pattern of additional proteins from the mitochondria during apoptosis, such as the ~26 KDa adenylate kinase (AK) were also examined (Single et al., Cell Death. Differ. 5, 1001-1003, 1998).

Figure 2C:
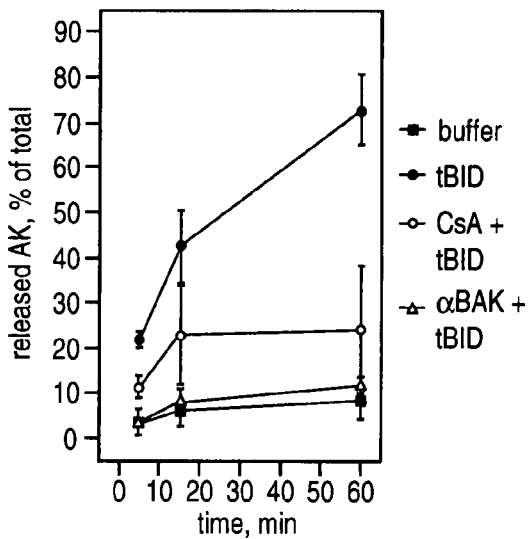

AK release was determined similar to that described for cytochrome c release. AK was quantified measuring its enzymatic activity by assessing the rate of NADH oxidation at 366 nm using a Beckman DU-10 spectrophotometer. 10 μl of the supernatant or pellet were added to a reaction mixture containing 0.5 mM phosphoenolpyruvate, ATP, AMP, 1 mM NADH, and 60 units of pyruvate kinase and lactate dehydrogenase, in 130 mM KCl, 6 mM MgSO$_4$ and 100 mM Tris-Cl. Final volume 0.1 ml, pH 7.4, 25° C. AK release is reported (as described for cytochrome c) as the percentage of the supernatant over the total (pellet plus supernatant).

tBID induced the release of AK, and anti-BAK antibody also completely inhibited that release. CsA substantially decreased but did not completely eliminate release of AK similar to the release of cytochrome c (FIG. 2C). Neither anti-BCL-X$_L$ antibody nor the broad specificity caspase inhibitor zVAD-fmk had any effect on tBID induced release of cytochrome c or AK. These results reveal that BAK oligomerization which is essential for tBID-induced cytochrome c release, still occurs in the presence of CsA. Consistent with this observation, some cytochrome c and AK is still released, yet substantial stores are retained indicating CsA blocks a significant component of the tBID pathway.

Figure 2D:
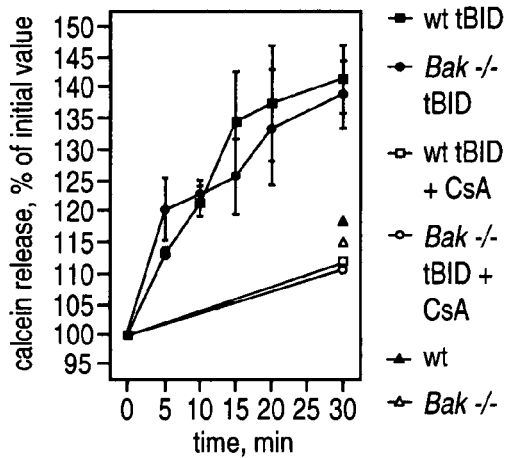

CsA blocked tBID induced transient opening of the PTP, but not BAK oligomerization or the initial release of cytochrome c, suggesting these processes are distinct. Therefore, the response of Bak-deficient mitochondria was determined. tBID did not induce significant cytochrome c release across the outer membrane of Bak −/− as contrasted to wt mitochondria (Wei et al., 2000). In contrast, tBID induced comparable CsA-inhibitable calcein release in Bak−/− as well as wt mitochondria (FIG. 2D). These data indicate that the tBID-induced calcein release is BAK independent, but is fully sensitive to CsA. Moreover, sustained flickering of the PTP is not secondary to the loss of cytochrome c since Bak−/− mitochondria don't release cytochrome c.

Example 3

Redistribution of Cytochrome c Upon tBID Treatment

The amount of cytochrome c released at 15 mins in the presence of tBID plus CsA was ~17% more than buffer alone (FIG. 2B), similar to the estimate (~16%) of cytochrome c that is resident in the IMS. The precise mechanism whereby the stores of cytochrome c within the cristae (~85%) are mobilized for release during apoptosis remained uncertain. Therefore, tBID was examined to determine whether induced redistribution of cytochrome c stores from the cristae to the IMS, where it would be available for release across the OM in a BAK-dependent fashion.

FIG. 3 shows the effects of BID on cytochrome c mobilization in wt and Bak −/− mitochondria. Panels 3A and 3B are a schematic of different intramitochondrial cytochrome c pools and their accessibility by cytochrome $b_5$ or ascorbate. Symbols used are detailed in the legend. Panel 3C shows representative traces of ascorbate driven respiration. 1 mg mitochondria were incubated with 200 nmol $Ca^{2+}$×mg protein$^{-1}$ (c), or with tBID (b and d). (a), no additions. In (d), mitochondria were preincubated for 2 min with 800 pmol CsA×mg protein$^{-1}$. After 15 min, mitochondria were treated with antimycin A and CCCP, transferred into a oxygen electrode chamber and after 2 min oxygen recordings were started. Arrow, 6 mM ascorbate-Tris and 300 µM TMPD were added.

Panel 3D shows the effects of tBID on the ratio of ascorbate over TMPD driven respiration in wt (black bar) and Bak −/− (gray bar) mitochondria. The experiments were conducted exactly as in (C). Data represent mean±S.D. of 3 different experiments.

Panel 3E shows representative traces of NADH fluorescence changes caused by cytochrome $b_5$-dependent NADH oxidation. 1 mg mitochondria were incubated with 200 nmol $Ca^{2+}$×mg protein$^{-1}$ (c and e), or with tBID (b and d). (d), mitochondria were preincubated for 2 min with 800 pmol CsA×mg protein$^{-1}$. (a), no additions. After 15 min, respiratory chain inhibitors were added and after another 2 minutes NADH fluorescence reading started. Arrow, 20 nmol NADH× mg protein$^{-1}$. In (e), 200 nmol mersalyl×mg protein was added 1 min before NADH.

Panel 3F is a time course of the effects of tBID on cytochrome $b_5$-dependent NADH oxidation. Wt (closed symbols) and Bak −/− (open symbols) mitochondria were incubated for the indicated time with tBID (circles and triangles). Triangles, mitochondria were pretreated with 800 pmol×mg protein$^{-1}$ CsA for 2 mins before the addition of tBID. Squares, no additions. Unless noted, data represent mean±S.D. of 3 different experiments.

Panel 3G shows the effects of tBID on the digitonin releasable cytochrome c pool in Bak −/− mitochondria. Mitochondria were treated with 80 pmol digitonin×mg protein$^{-1}$ for 5 mins after incubation with tBID for 45 mins if noted. Where indicated, mitochondria were pretreated with 800 pmol CsA× mg protein$^{-1}$ for 3 mins prior to the addition of tBID. Panel 3H shows the effects of a G94E BID mutant on cytochrome $b_5$-dependent NADH oxidation. The experiment was performed as in (F), except that wt (closed circle) and G94E (open circle) p7/p15 caspase cleaved BID complex was used.

Assays were developed to assess the amount of cytochrome c freely available in the IMS (FIGS. 3A, B). In the ascorbate/TMPD-driven respiration assay 1 mg/ml mitochondria were incubated in sucrose buffer (0.2 M sucrose, 10 mM Tris-MOPS pH 7.4, 1 mM Pi, 5 mM glutamate, 2.5 mM malate, 10 µM EGTA-Tris, pH 7.4) and treated as indicated in the Fig. legends. After the indicated time, 400 pmol CCCP and 1 nmol antimycin A×mg protein$^{-1}$ were added, and the reaction transferred to a Clark type oxygen electrode chamber. Final volume was 1 ml, 25° C. After 2 min, 6 mM ascorbate was added, followed after a further 3 min by 300 µM TMPD. The ascorbate-driven $O_2$ consumption rate over the total TMPD-driven rate is plotted as a percentage of the ratio in the untreated mitochondria.

Ascorbate is capable of reducing only free cytochrome c, whereas the uncharged reductant TMPD is membrane permeable and diffuses widely to reach all cytochrome c (Nicholls, et al., Can. J. Biochem. 58, 969-977, 1980). Consequently, the ratio of ascorbate-driven respiration over the total TMPD-driven respiration (ascorbate/TMPD) would be expected to increase if cytochrome c was mobilized. In support, unfolding of the cristae caused by $Ca^{2+}$ mediated swelling increases the ascorbate-driven respiration (FIG. 3C). tBID caused a substantial increase in ascorbate driven respiration at 15 mins that was blocked by pretreatment with CsA (FIGS. 3C, D). This increase occurred independently of BAK (FIG. 3D). These results indicate tBID treatment dissociates cytochrome c from its ascorbate-inaccessible sites.

The accessibility of cytochrome c to the OM by measuring the effects of tBID on cytochrome $b_5$ mediated NADH oxidation was quantitated (FIGS. 3A, B). Cytochrome $b_5$ is an OM protein that transfers electrons from a NADH dehydrogenase, accessible to exogenous (i.e. extramitochondrial) NADH, to cytochrome c (Lehninger, J. Biol. Chem. 190, 345-359, 1951; Bernardi and Azzone, 1981). The availability of cytochrome c is rate limiting for this reaction. The NADH oxidation rate increases when more cytochrome c is available to cytochrome $b_5$, reflecting more cytochrome c present in the IMS (Bernardi and Azzone, 1981).

In the cytochrome $b_5$-dependent NADH oxidation assay, 1 mg/ml mitochondria were incubated in EB and treated as indicated. 400 pmol CCCP, 2 nmol rotenone and 1 nmol antimycin A×mg protein$^{-1}$ were added after the time indicated and the reaction transferred to a cuvette. After 2 min, 10 µM NADH was added and its oxidation monitored as the decrease in NADH fluorescence in a LS50B spectrofluorimeter (Perkin Elmer) set with $\lambda_{ex}$=366 nm and $\lambda_{em}$=455 nm, with 5 nm slits.

As the model predicts (FIGS. 3A, B), treatment of mitochondria with $Ca^{2+}$ increased the rate of NADH oxidation, as a consequence of cristae unfolding that accompanies mitochondrial swelling (FIGS. 3B, E). The NADH oxidation in this assay is completely dependent on cytochrome $b_5$, since assays were performed in the presence of the complex I inhibitor rotenone, and all increases proved totally inhibited by the cytochrome $b_5$ inhibitor mersalyl (Bernardi and Azzone, 1981) (FIGS. 3A, E). tBID also increased the NADH oxidation rate, which proved fully inhibitable by CsA (FIG. 3E). Next, cytochrome $b_5$-dependent NADH oxidation in Bak −/− mitochondria was examined. tBID induced a comparable, CsA inhibitable, increase in cytochrome $b_5$-dependent NADH oxidation in BAK-deficient mitochondria (FIG. 3F). This similar increase in wt and Bak −/− mitochondria eliminates the possibility that the released cytochrome c might accept electrons at the cytochrome $b_5$ site.

Whether tBID would increase the amount of cytochrome c available for release was assessed by detergent permeabilization of the OM of Bak−/− mitochondria. Treatment of Bak−/− mitochondria with a concentration of digitonin that does not interfere with IM function caused the release of 19.2±4.8% of total cytochrome c (FIG. 3G). Pretreatment of Bak −/− mitochondria with tBID increased the amount of cytochrome c released to levels comparable to that of wt mitochondria. This tBID induced mobilization was also CsA inhibitable (FIG. 3G). Thus, three assay systems indicate that tBID causes a BAK independent mobilization of cytochrome c that increases its availability for release across the OM.

Example 4

Induction of Mitochondrial Cristae Remodeling by tBID

The physiological assays employed above identified a tBID induced redistribution of cytochrome c, presumably from the cristae into the IMS. This BAK-independent, CsA inhibitable redistribution of cytochrome c is distinct from the release of cytochrome c across the OM as BAK-deficient mitochondria redistribute, but do not release cytochrome c. To determine if structural changes to mitochondria accompanied these physiologic measurements of cytochrome c mobilization, transmission electron microscopic (TEM) images were collected.

FIG. 4 is a transmission electron micrograph (TEM) showing tBID treated wt and Bak −/− mitochondria. wt (Panels 4A-C) and Bak −/− (Panels 4D-F) mitochondria (0.5 mg) were incubated with tBID for 5 min (Panels B, C and E, F). In the experiments of (C) and (F), mitochondria were pretreated for 2 min with 800 pmol×mg protein$^{-1}$ CsA. Bar, 500 nm. Representative mitochondria with Class I morphology (arrowhead) and Class II morphology (arrow) are noted.

For these experiments, mitochondria were fixed for 1 h at 25° C. using glutareldehyde dissolved in EB at a final concentration of 1.25%, embedded in plastic, sectioned, and stained with uranyl acetate and lead citrate. Thin sections were imaged on a JEOL 1200EX transmission electron microscope. For tomography, colloidal gold particles were applied to one side of 300-500-nm-thick sections as alignment markers. Tilt series of 122 images were recorded on the Albany AEI EM7 MkII HVEM, operated at an acceleration voltage of 1000 kV. The images were recorded around two orthogonal tilt axes, each over an angular range of 120° with a 2° tilt interval. The double-tilt images were aligned as previously described (Penczek et al., Ultramicroscopy 60, 393-410, 1995) and tomographic reconstructions were made using the weighted back-projection method (Radermacher, In Electron Tomography, pp. 91-115, 1992). Image processing was done using the SPIDER system. The reconstructed volumes had dimensions of 512×512×100-145 pixels depending on section thickness, with a pixel size range of 2.5-4.1 nm. Surface-rendered models were made using Sterecon (Marko and Leith, J. Struct. Biol. 116, 93-98, 1996) to segment the volume and Iris Explorer (NAG, Downers Grove, Ill.) for rendering. Measurements of the dimensions of cristae openings were made directly on 1-pixel-thick slices from the respective tomograms.

Figure 5A:
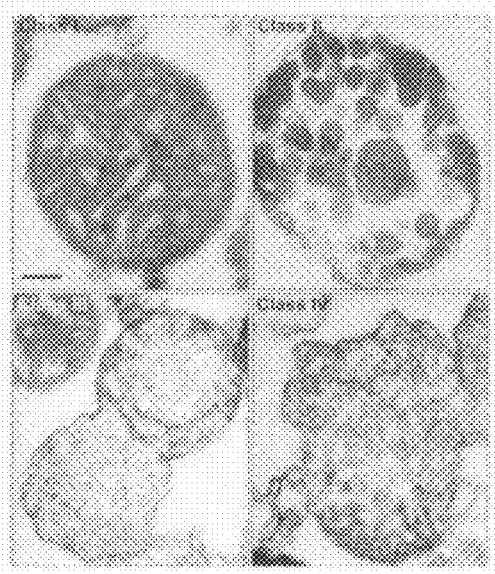
FIG. 5 is a photograph of a transmission electron micrograph and corresponding bar graphs showing morphometric analysis of tBID effects on wt and Bak −/− mitochondria.

Purified normal mitochondria in the presence of respiratory substrates display a partially condensed conformation that is referred to as Class I morphology, with numerous, narrow pleomorphic cristae (appearing in transmission EM as small electron transparent areas) in a contiguous electron dense matrix space (FIGS. 4A, D; 5A). tBID treated mitochondria display a series of morphological changes. The majority of the mitochondrial population appears to be in a remodeled state that is denoted as Class II, characterized by a serpentine electron transparent intracristal compartment interrupted by electron dense matrix spaces (FIGS. 4B, E; 5A). The electron dense matrix often appears circular and, depending on the orientation of the thin section, can be organized to resemble an "intestinal" or "sausage-shaped" electron dense region. Remodeled Class II mitochondria differ from the condensed mitochondria described by Hackenbrock during stimulated (State 3) respiration (Hackenbrock, J. Cell Biol. 30: 269-297, 1966), in that the cristae and matrix spaces are markedly reorganized. Moreover, addition of excess ADP to our isotonic respiratory buffer did not cause the appearance of Class II mitochondria. A few tBID treated mitochondria have progressed to gross morphological derangement entitled Class III, with asymmetric blebbing of herniated matrix resulting in a partial rupture of the OM and swelling on one side of the mitochondrion (FIG. 5A). A Class IV designation was assigned to a terminally swollen and ruptured mitochondrion with little or no distinguishable cristae structure (FIG. 5A). The mean calculated area of 100 measured Class II mitochondria was comparable to that of 100 Class I mitochondria (2.14 vs. 2.38 µm$^2$; ANOVA test, ns), arguing that as a population they are not swollen. These same stages are also observed in tBID treated Bak −/− mitochondria (FIG. 4E). However, pretreatment with CsA inhibits the appearance of these abnormalities (FIGS. 4C, F).

Since both the redistribution of cytochrome c and its release across the OM are functions of time, morphometric analysis on mitochondria over a time course following addition of tBID was performed. For morphometric analysis of fields of mitochondria in thin sections, at least 4 different transmission EM micrographs representing different areas in the grid were selected and number-coded prints were produced. Mitochondria with profile diameters <200 nm were excluded from the analysis, and in the case of mitochondria which displayed characteristics bridging morphologic classes they were assigned to the lower class. The classification procedure was performed in a blinded fashion.

Figure 5B:
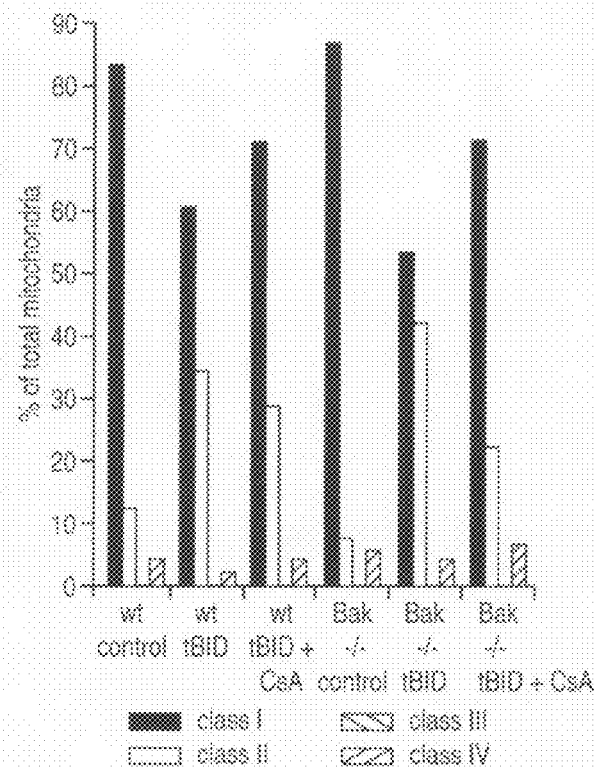
Figure 5C:
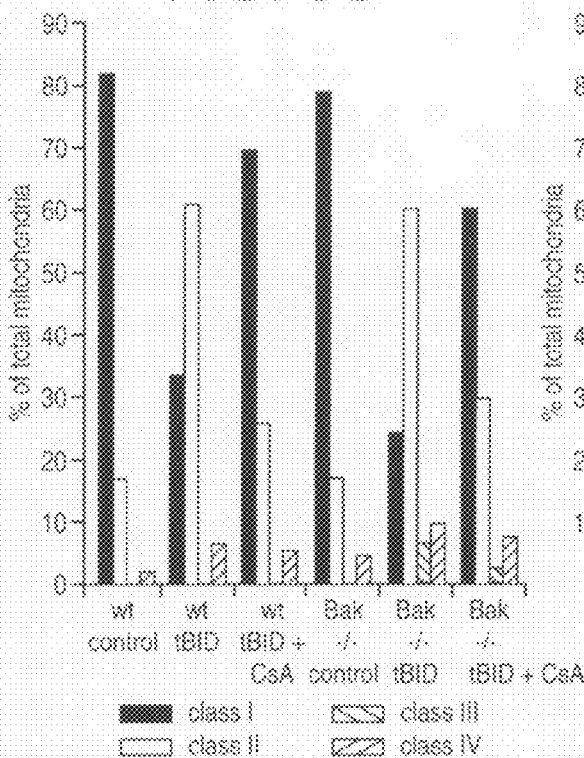
Figure 5D:
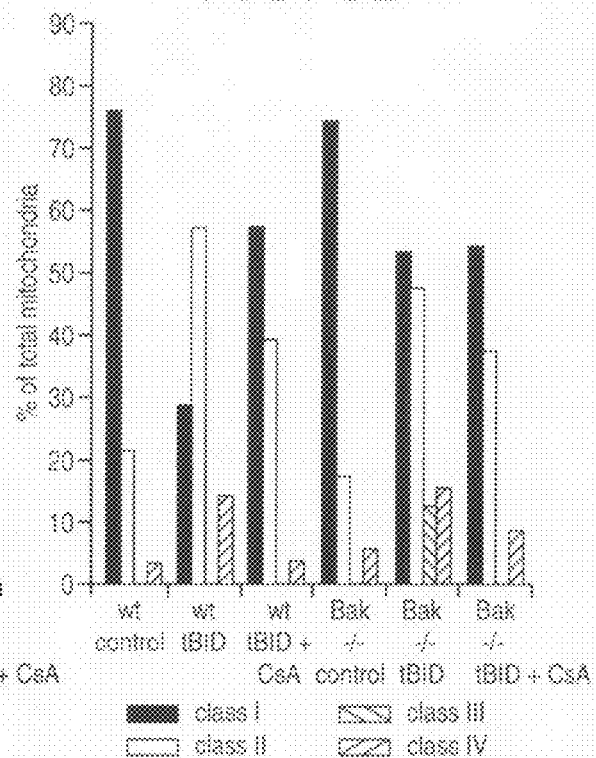

FIG. 5 shows morphometric analysis of tBID effects on wt and Bak −/− mitochondria. Panel 5A is a representative TEM of Class I-IV mitochondria. Panels 5B-5D show morphometric analysis of mitochondria. Where indicated, 0.5 mg wt and Bak −/− mitochondria were incubated with tBID. Where indicated, mitochondria were pretreated for 2 min with 800 pmol×mg protein$^{-1}$ CsA. After 2 (B), 5 (C), and 10 mins. (D) mitochondria were fixed, and TEM images were taken. Morphometric analysis was performed and mitochondria were assigned to morphological Classes I-IV.

tBID induced a shift in mitochondrial morphology from Class I to Class II within 2 mins, and by 5 mins Class II mitochondria predominate (FIGS. 5B, C). At later time points, Class III and Class IV mitochondria appear in-vitro (FIG. 5D). While this tBID induced morphologic progression also occurs in the absence of BAK, it is inhibited by treatment with CsA (FIG. 5). Overall, the time course of appearance of Class II mitochondria temporally correlates with the redistribution of cytochrome c and both proved sensitive to CsA.

To determine whether Class II morphology could account for the increased availability of cristae stores of cytochrome c required a three-dimensional reconstruction of such mitochondria. High voltage electron microscopy (HVEM) and tomographic reconstruction was performed on thick sections of mitochondria as described above.

FIG. 6 is electron microscopy tomography showing representative Class I, II and III mitochondria. Representative cross sectional slice of electron microscopic tomogram of selected Class I (6A), Class II (6B) and Class III (6C) mitochondrion. Surface rendered views of tomographic reconstructions of each class are shown in A', B', C', respectively. The OM is depicted in red, the inner boundary membrane in yellow, and the cristae in green. Note that representative, selected cristae were traced in the Class I and III mitochondrion as they were distinct. However, in the Class II mitochondrion the highly interconnected cristae network had to be entirely traced. In panels A", B", and C", the representative tomographic reconstructions are rotated 90° to depict the level of cristae junctions with the inner membrane boundary. Arrows indicate select cristae junctions. The dimensions of the mitochondrial reconstructions (diameter×thickness) are (A) 930 nm×360 nm, (B) 860 nm×450 nm, (C) 1600 nm×310 nm.

Figure 6A:
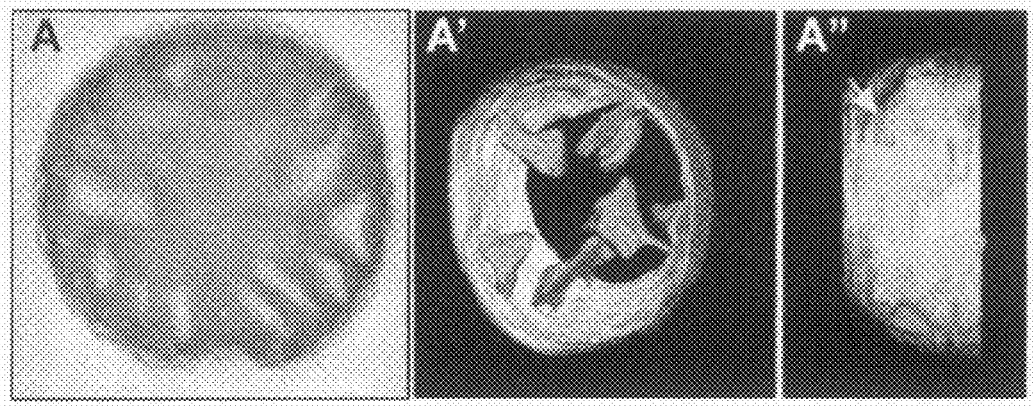
FIG. 6 is a photograph of an electron microscopy tomograph showing representative Class I, II and III mitochondria.

The pleomorphic cristae are connected to the inner boundary membrane by narrow, tubular junctions in Class I mitochondrion (FIG. 6A'). In contrast, in Class II mitochondrion the cristae compartment undergoes a dramatic remodeling. The individual cristae appear fused into what is perhaps a single or a few large compartments (FIG. 6B') and the cristae junctions are widened markedly. The "crowded" appearance inside Class II mitochondrion is due to the extreme interconnectivity of the intracristal space, which was documented during the tracing and rendering procedure. Moreover, the curvature of the IM that outlines the cristae is frequently concave facing the matrix in Class II but convex in Class I mitochondria. The relative volume occupied by the matrix space versus the intracristal space was computationally estimated (SPIDER) from the tomograms of reconstructed Class I and II mitochondria. Matrix space accounted for 75-80% of the total volume of the Class I compared to 80-85% of the Class II mitochondrion, providing further evidence that the remodeling of the latter is not simply a condensed, hypercontracted state.

Figure 6B:
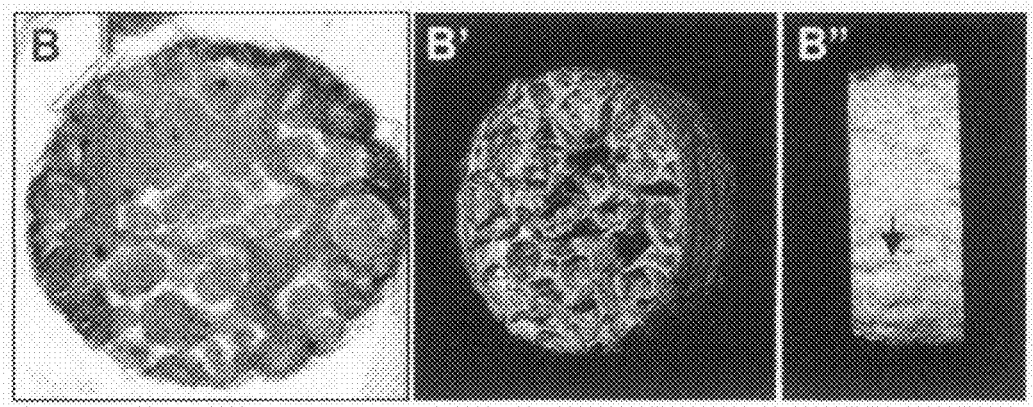
Figure 6C:
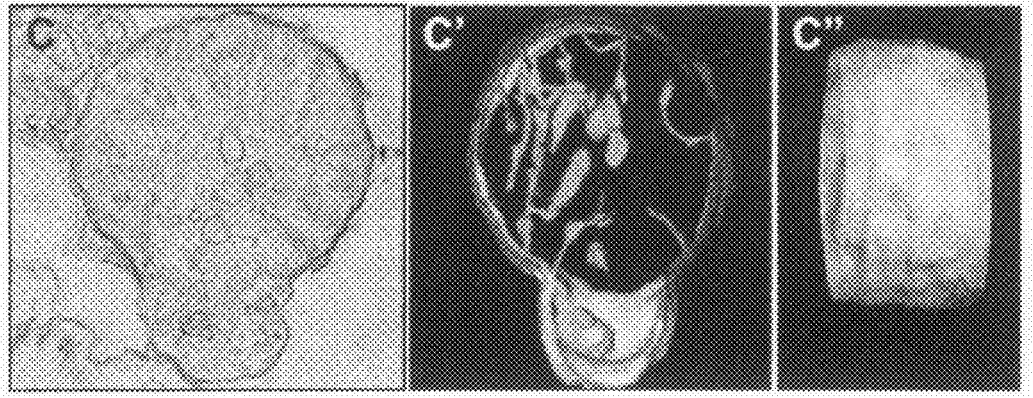

Rotation of EM tomographic reconstructions reveal the cristae junctions at the level of the inner membrane boundary which are presented in FIG. 6A", B", C". Measurements indicate the average diameter of cristae junctions is 18.6±2.5 nm for Class I mitochondria (FIG. 6A", yellow arrow) which has expanded to extremely elongated, ellipsoidal openings of 56.6±7.7 nm, (p=0.008 Student's t test; range up to 71 nm) in Class H mitochondria (FIG. 6B", blue arrow). Reconstructed Class III mitochondria reveal an asymmetric herniation of matrix which distends the IM on one side with rupture of the OM at that site. Cristae structures are lost in the herniated region where the IM has unfolded (FIG. 6C'). The remaining cristae junctions also provide a wider opening between the cristae and the IM (FIG. 6C", blue open arrow).

Example 5

Evaluation of Class II Mitochondria Remodeling Following Diverse Apoptotic Signals In intact cells, two "multidomain" proapoptotic molecules BAK and BAX are utilized to release cytochrome c from mitochondria following multiple apoptotic stimuli (Wei et al., 2001). Thus, Bax, Bak-doubly deficient (DKO) cells provide an opportunity to investigate the occurrence of Class II mitochondria in-vivo following diverse death stimuli and assess their dependence on BAK, BAX.

For apoptosis induction, MEFs were plated in 24-well plates at a density of $10^4$ cells/well and grown for 24 hrs (Wei et al, 2001). Apoptosis was initiated by 2 μM thapsigargin, 2 μg/ml brefeldin A, 1 μg/ml tunicamycin or by 5 hrs of heat shock (43° C. in a humidified atmosphere of 95% air 5% $CO_2$). Apoptosis was detected by flow cytometric detection of annexin V staining (BD Pharmingen) 24 hrs after the induction of cell death.

TEM performed 12 hrs. following treatment with thapsigargin, tunicamycin, brefeldin A or heat shock revealed frequent mitochondria with Class II morphology in DKO as well as wt cells. FIG. 7 shows mitochondrial morphology and morphometry in Wt and Bax, Bak-deficient cells primed for apoptosis. Panel 7A shows TEM images of mitochondria in wt and Bax, Bak-deficient cells (DKO). Wt and DKO MEFs were treated where indicated with brefeldin A or heat shock. After 12 hrs cells were fixed and imaged. Bar, 200 nm. The insets show 2× magnification of the boxed mitochondria. Panel 7B shows morphometric analysis of mitochondria in-vivo cells following death stimuli. Wt and DKO MEFs were treated with the indicated death stimulus and after 12 hrs cells were fixed, stained and TEMs collected. Morphometric analysis was conducted.

The Class II mitochondria are nearly identical to those noted in purified mitochondria with remodeled cristae compartments interrupted by circularized electron dense matrix. Morphometric analysis revealed that BAX, BAK DKO cells, which are resistant to these signals, demonstrated a predominance of Class II mitochondria similar to wt cells (FIG. 7B). Thus, Class II mitochondria were prominent in cells following several intrinsic death stimuli, and as observed in vitro, the mitochondrial remodeling occurred independent of BAX, BAK. It is conceivable that during apoptosis two parallel mitochondrial pathways operate, one to guarantee release of cytochrome c across the OM, the other to remodel mitochondria to ensure the completeness of this release.

Example 6

Evaluation of the BH3 Domain of tBID on Cytochrome c Release

Figure 2E:
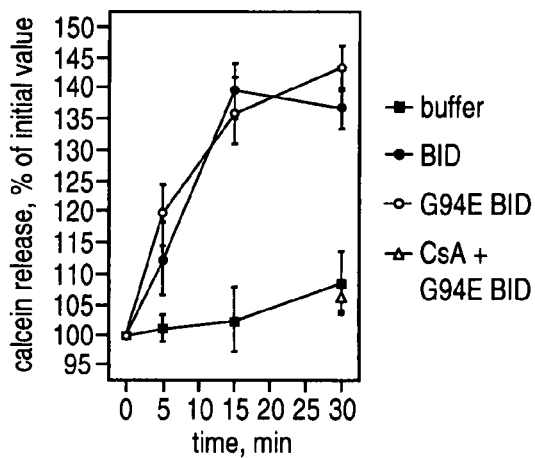

The conserved amphipathic α helical BH3 domain is required for the full biologic activity of the "BH3 only" molecules, such as tBID. tBID requires an intact BH3 domain to bind BAK, induce the oligomerization of BAK and release cytochrome c (Wei et al., 2000). The BH3 mutant BID G94E that targets mitochondria but fails to release cytochrome c was tested for its ability to induce transient opening of the PTP. BID G94E proved as effective as wt BID in inducing the release of calcein (FIG. 2E). Moreover, examination of cytochrome $b_5$-dependent NADH oxidation indicates that mutant G94E increased cytochrome c accessibility to the OM nearly as well as wt BID (FIG. 3H). This provides further evidence that the release of cytochrome c across the OM (BH3 dependent) is a separable pathway from the mobilization of cytochrome c (BH3 independent). Moreover, it indicates that a region of tBID beyond BH3, likely an intramembranous portion, is responsible for triggering the mobilization of cytochrome c.

The observed remodeling of the inner membrane associated with mobilization of cytochrome c is generally consistent with previous reports of mitochondrial ultrastructural changes in early stages of apoptosis (Sheridan et al., J. Cell Sci. 49:119-37., 119-137, 1981; Mancini et al., J. Cell Biol. 138, 449-469, 1997). However, the remodeling of the inner membrane noted here (such as changes in the shape of cristae junctions) could easily be missed in the absence of 3D tomographic analysis. Consistent with this morphologic change, functional studies revealed that the entire population of cytochrome c was now accessible at the OM for cytochrome $b_5$ driven redox reactions. It is possible that Class II mitochondria represent a decisive step which enables the complete release of cytochrome c and the onset of mitochondrial dysfunction, essential for many death stimuli.

Increased accessibility of cytochrome c to the OM was previously noted following $Ca^{2+}$ induced mitochondrial swelling (Bernardi and Azzone, 1981). tBID in contrast induced redistribution in the absence of swelling and independent of BAK, indicating that actual release of cytochrome c across the OM was not required for remodeling. Attardi and co-workers noted that only cells primed for apoptosis by Fas activation released all stores of cytochrome c upon selective permeabilization of the OM by digitonin (Hajek et al., J. Biol. Chem. 276, 606-615, 2001). While tBID did not induce large amplitude mitochondrial swelling, it did induce transient openings of the PTP. Transient openings have been noted in isolated mitochondria and intact cells, and are not associated with swelling or $\Delta\psi_m$ collapse (Huser et al., Biophys. J. 74, 2129-2137, 1998; Petronilli et al., Biophys. J. 76, 725-734, 1999). This transient PT was coordinate with cristae remodeling and cytochrome c mobilization as both proved BH3 independent, BAK independent, yet CsA inhibitable. This parallel regulation suggests a common mechanism or a shared component. It has been suggested that components of the PTP reside at contact points between IM and OM (Zoratti and Szabo, Biochim. Biophys. Acta 1241, 139-176, 1995). While the mobilization of cytochrome c would have no obvious need to involve such contact points, the striking remodeling of cristae strongly suggests tBID has an effect on the IM. Alterations at OM/IM contacts affects the opening of cristae junctions and the changes to IM curvature noted in Class II mitochondria. The capacity of CsA to block this process suggests that its mitochondrial target, cyclophilin D (Nicolli et al., J. Biol. Chem. 271, 2185-2192, 1996) could be a functional component of this remodeling process. Alternatively, a CsA/cyclophilin D complex might affect another mitochondrial protein by analogy with the mechanism by which CsA inhibits cytosolic calcineurin (Clipstone and Crabtree, Nature 357, 695-697, 1992). Recently dynamin family proteins, large GTPases that generate mechanoenzymatic force on membranes, have been localized to mitochondria and shown to participate in the maintenance of mitochondrial shape including the dynamic process of fission and fusion (Margolin, Curr. Biol. 10, R328-R330, 2000). Proteins that control mitochondrial shape are candidates for the apoptotic pathway (Frank et al., Dev. Cell 1, 515-525, 2001) given the dramatic reorganization of IM in Class II mitochondria. Overall, while tBID's initial target BAK mediates release of cytochrome c across the OM, we propose tBID has a second role or alternative target that mediates cristae remodeling.

The pathway of mitochondrial remodeling and transient PT initiated by tBID is genetically distinct from the actual release of cytochrome c across the OM, which requires BH3 of BID and the presence of BAK, but is resistant to CsA.

Figure 8:
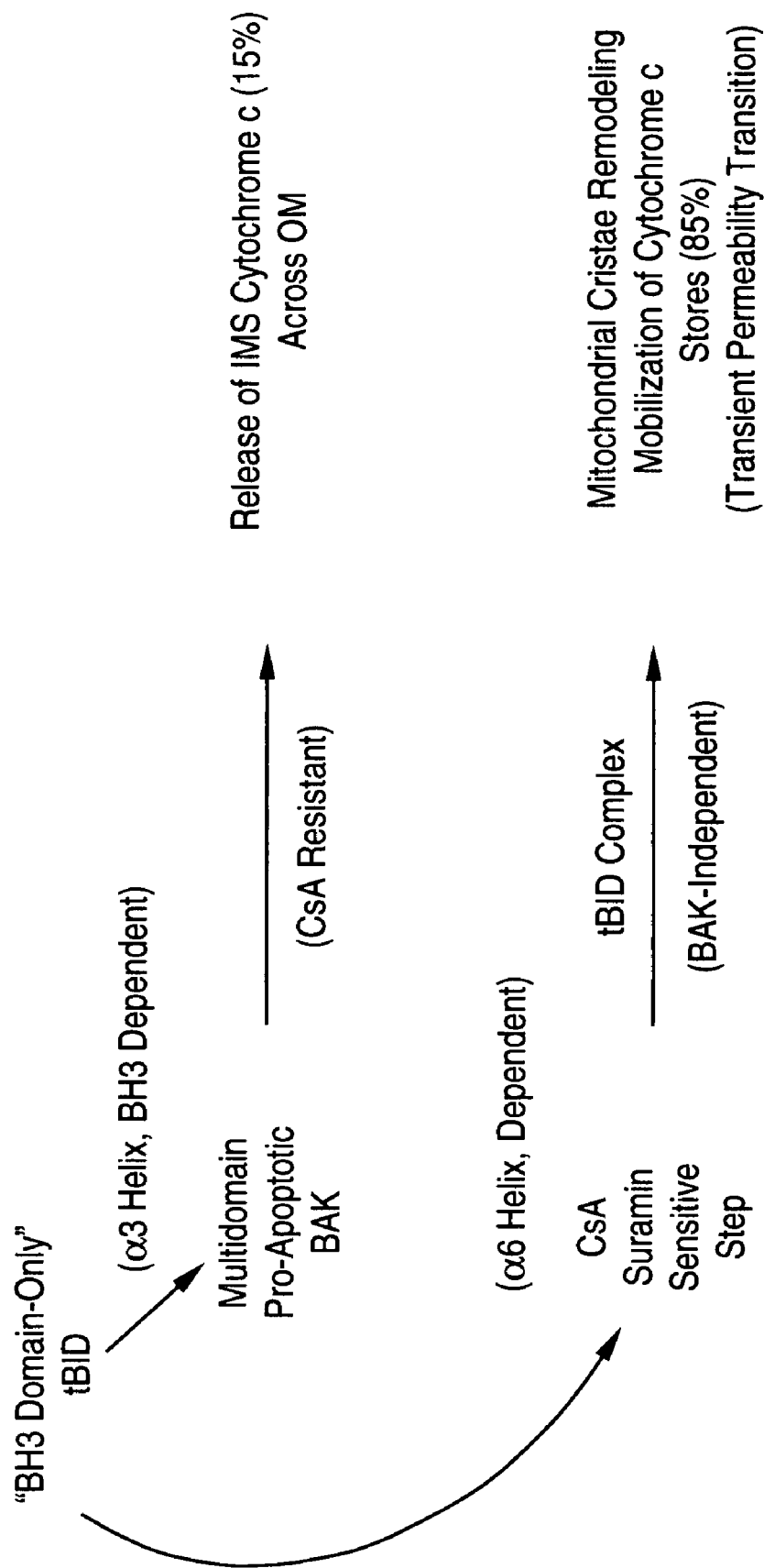
FIG. 8 is a schematic that diagrams two distinct pathways downstream of a "BH3 domain-only" tBID signal.

FIG. 8 is a schematic that diagrams two distinct pathways downstream of a "BH3 domain-only" tBID signal. One pathway requires the α3 helix (BH3 domain) of tBID, is BAK-dependent, is resistant to cyclosporin A (CsA), and leads to the release of 15% of cytochrome c from the inner membrane space (IMS) across the outer membrane (OM). A second pathway is dependent on the α6 helix, is independent of BAK, is sensitive to CsA and suramin, and leads to mitochondrial cristae remodeling and mobilization of 85% of cytochrome c.

Thus the apoptotic pathway bifurcates following activation of a "BH3 only" molecule with activation of BAX, BAK resulting in the cytosolic release of cytochrome c and consequent caspase activity; whereas, a separate path of mitochondrial remodeling insures complete release of cytochrome c and mitochondrial dysfunction.

Example 7

Mobilization of Cytochrome c by a tBID α6 Helix Domain

Distinct genetic pathways are responsible for the redistribution of cytochrome c stored in intra-mitochondrial cristae or its release across the outer mitochondrial membrane. tBID triggered the initial release of cytochrome c (~15%) that resides in the IMS, which proved dependent on the oligomerization of BAK, but resistant to CsA. tBID also induced a striking remodeling of mitochondria structure with mobilization of the cytochrome c (~85%) stored in cristae, which did not require BH3 domain of tBID, proved independent of BAK, yet inhibitable by CsA. Electron microscopy with tomographic reconstruction defined distinct stages of mitochondrial reorganization, including a critical step where individual cristae fuse and the tight cristae junctions with the IMS open.

Since the α3 helix, BH3 domain, of tBID was not responsible for the pathway of cytochrome c mobilization and remodeling of the mitochondrial inner membrane other areas of BID were examined to identify the responsible domain. The α6 helix of BID was determined to be critical for this function.

Figure 9:
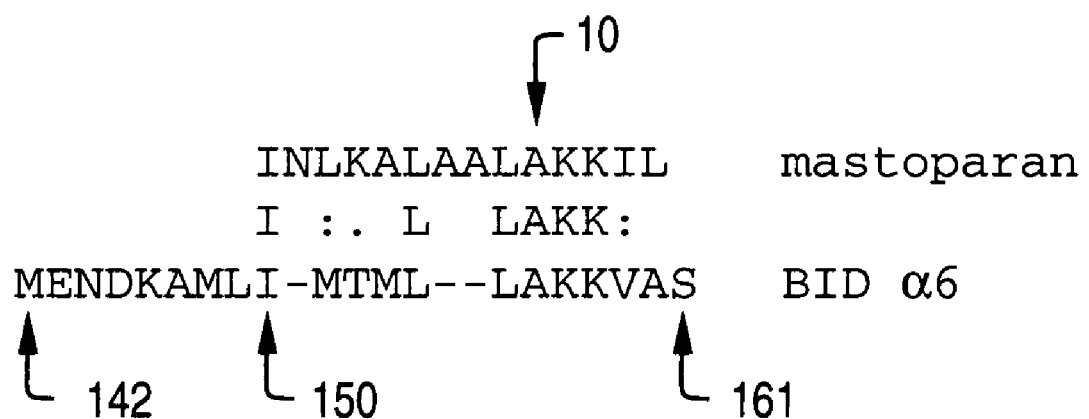
FIG. 9 is a schematic alignment showing the amino acid sequence comparison between the α6 helix of BID (SEQ ID NO: 10) and mastoparan (SEQ ID NO: 11).

FIG. 9 is a schematic alignment showing the amino acid sequence comparison between the α6 helix of BID and mastoparan. The BID α6 helix, $_{142}$MENDKAMLIMTML-LAKKVAS$_{161}$ (SEQ ID NO: 10), shares homology with mastoparan, $_1$INLKALAALAKKIL$_{14}$ (SEQ ID NO:11), a G protein activator. Dots indicate conservative amino acid differences.

Figure 10:
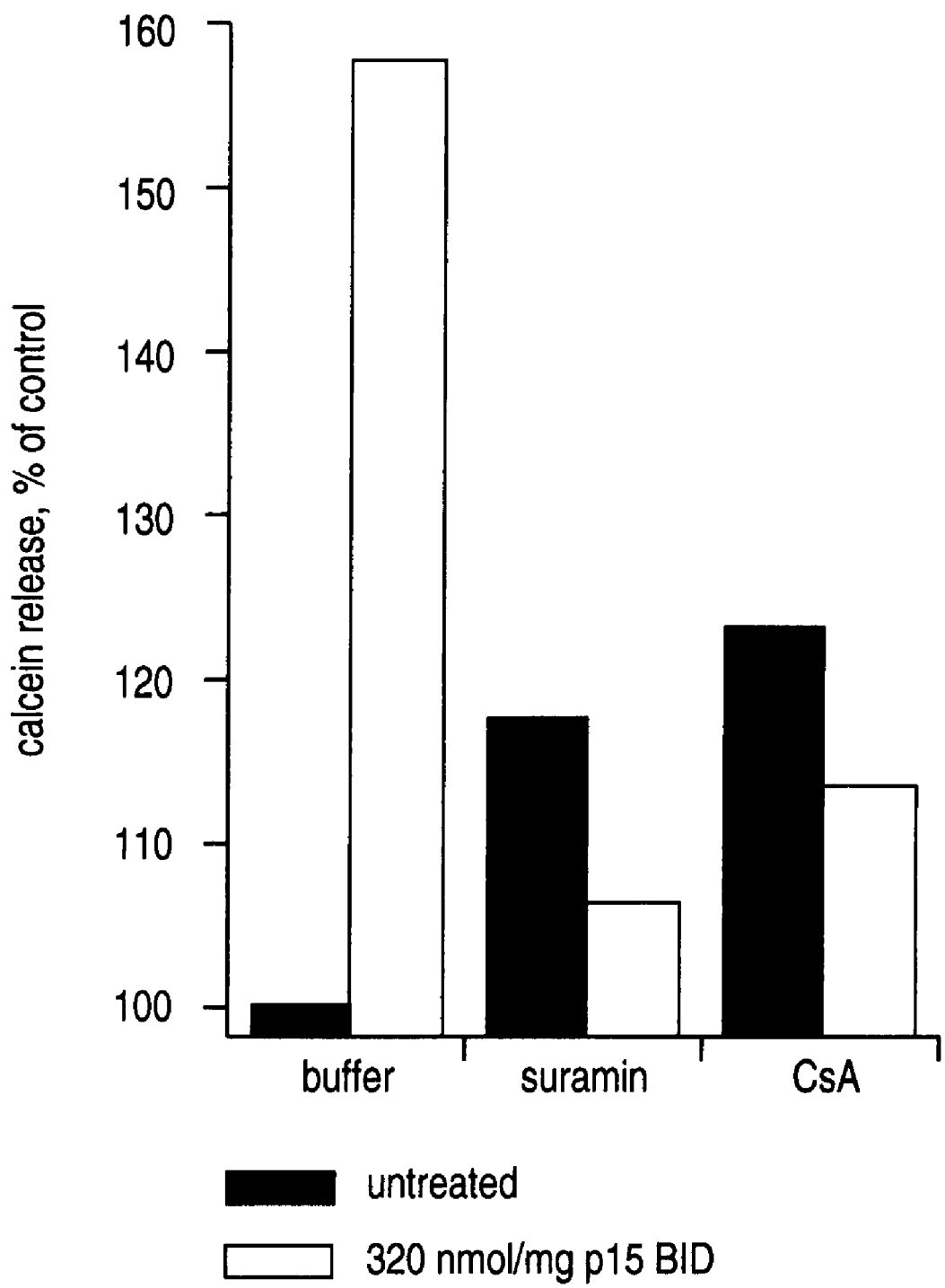
FIG. 10 is a bar graph showing that the G protein inhibitor suramin specifically inhibits calcein release induced by tBID.

To determine if BID α6 shares any function similarity to mastoparan, a G protein inhibitor (Suramin) was used in combination with tBID. Suramin has been shown to block tBID-induced transient permeability transition. FIG. 10 shows mitochondria loaded with calcein were incubated with 320 pmol/mg tBID or left untreated. Where indicated, mitochondria were preincubated for 3 min with 200 nmol/mg suramin, a concentration that does not inhibit the mitochondrial respiratory chain, or 800 pmol/mg CsA. After 30 min mitochondria were spun at 14000 g for 3 min at 4 C and the calcein content in the pellet and in the supernatant was determined. The results show that suramin blocked tBID-induced transient permeability transition (PT) providing further evidence for a G protein mediated pathway. Mutagenesis of the BID α6 helix revealed a critical intra-membranous motif that was responsible for the mitochondrial inner membrane remodeling. To determine if a BID α6 mutation variant, BID α6 mutein (SEQ ID NO:7), would inhibit cytochrome c release, His-tag p22 wt BID and the BID α6 mutein were expressed, purified on a $Ni^{2+}$ column, and cleaved with caspase 8.

Figure 11:
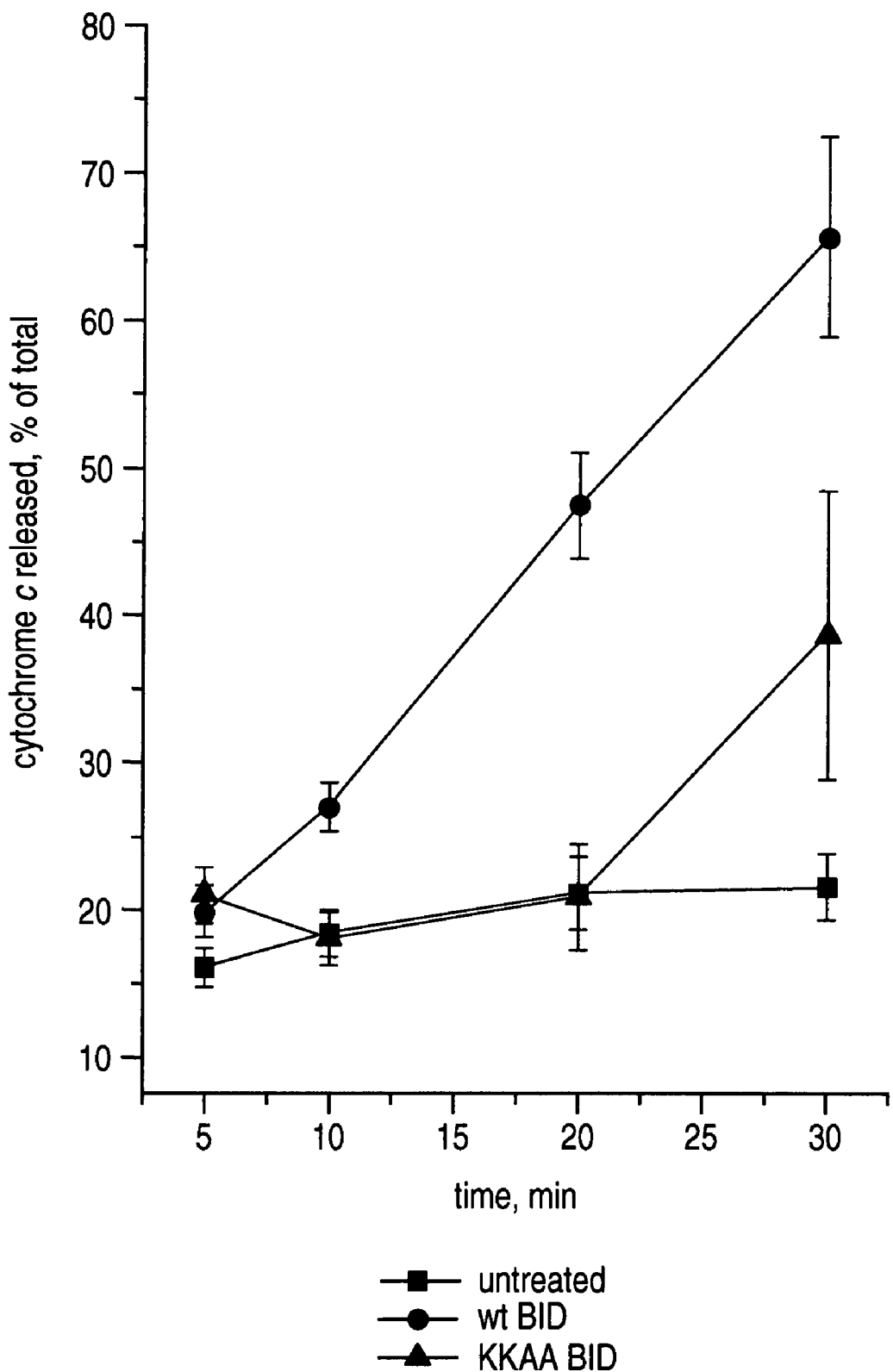
FIG. 11 is a line graph showing that BID α6 mutein does not completely release cytochrome c.
Figure 12:
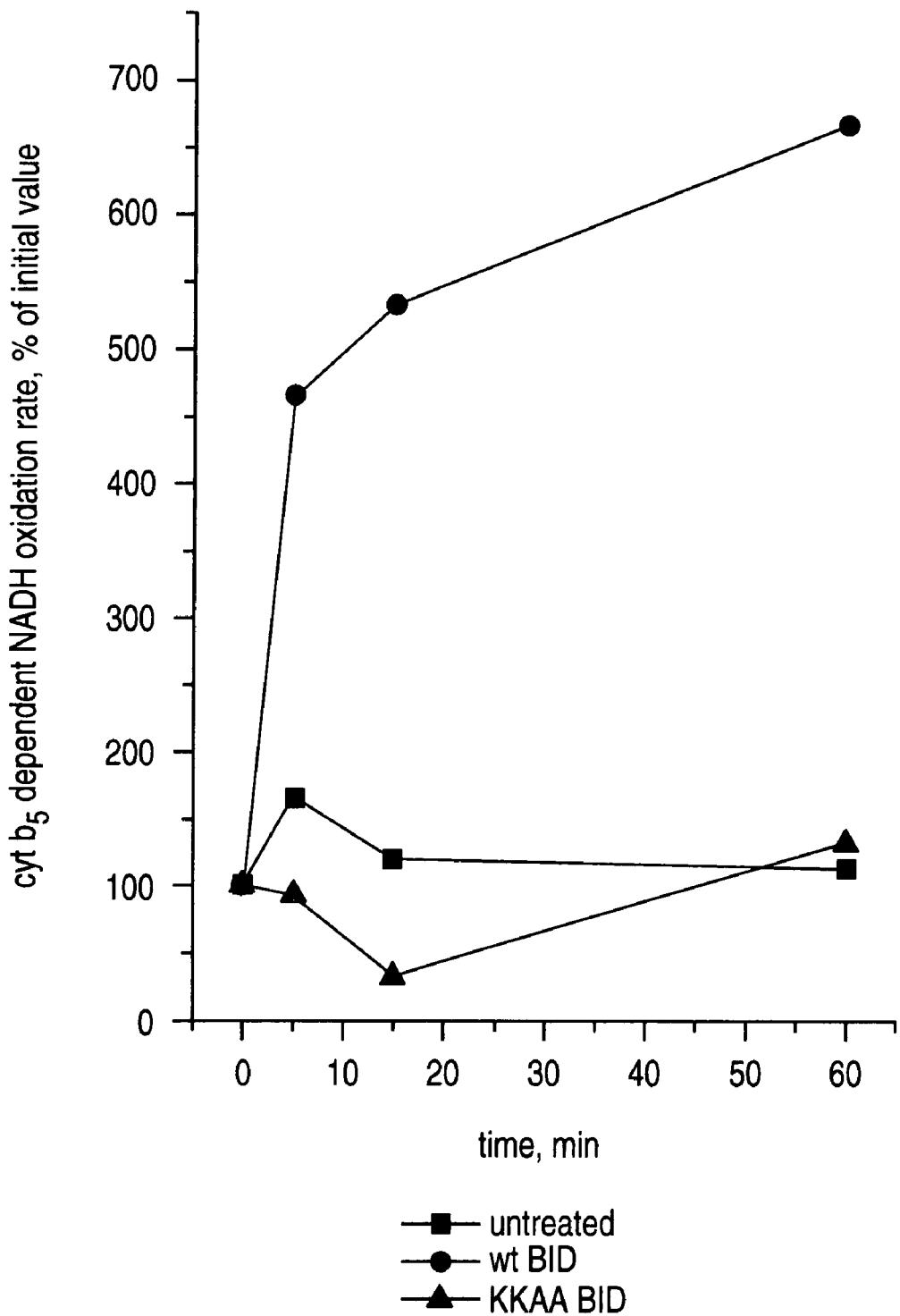
FIG. 12 is a line graph showing that BID α6 mutein fails to mobilize cytochrome c.

FIG. 11 shows that BID α6 mutein does not completely release cytochrome c. Mitochondria (0.5 mg) were left untreated or treated with 1.6 pmol wt p7/p15 BID or BID α6 mutein p7/p15 caspase cleaved BID×mg protein$^{-1}$. After the indicated time, mitochondria were pelleted and cytochrome c content in the pellet and in the supernatant was determined. Treatment of the mitochondria with BID α6 mutein (SEQ ID NO:7), where two lysine residues were changed to alanine residues, resulted in the impaired release of cytochrome c from mitochondria, releasing only ~20%, an amount consistent with the release of IMS stores, but suggesting the cristae based stores had not been mobilized. To confirm this result, 1 mg mitochondria were treated for the indicated time with wt p7/p15 BID or BID α6 mutein and then cytochrome b5-dependent NADH oxidation rate was determined. Comparing BID α6 mutein to wt tBID in the cytochrome b5-dependent NADH oxidation assay indicated that cytochrome c had not been mobilized (FIG. 12).

Figure 13:
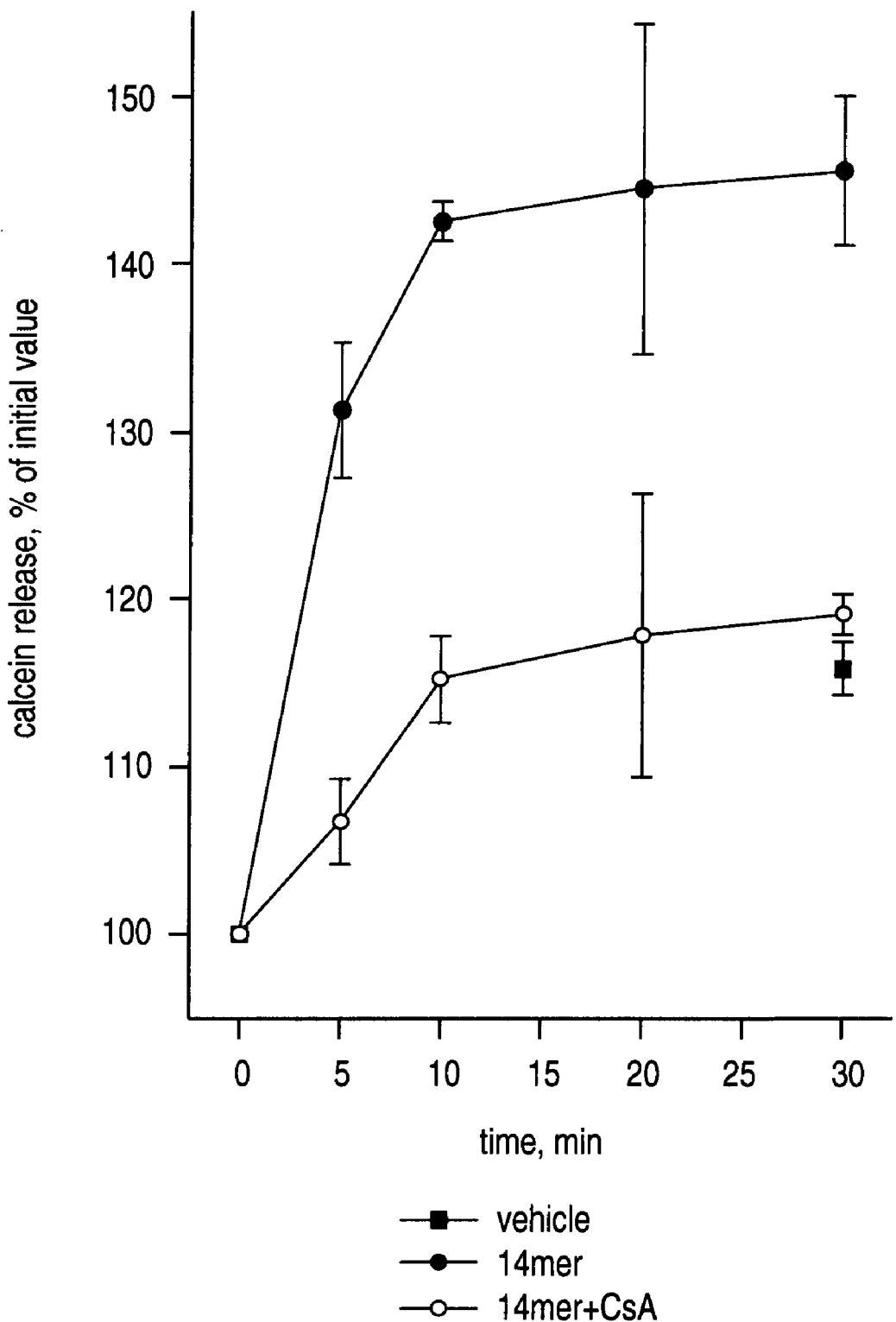
FIG. 13 is a line graph showing that BID α6 14mer causes calcein release from mitochondria.

Since the α6 intramembranous helix of tBID was required for cytochrome c mobilization, the ability of an α6 helix peptide to recapitulate this effect was examined A BID α6 14mer, (SEQ ID NO:1) was generated and purified to assess the ability of this peptide to initiate a program of mitochondrial remodeling and dysfunction. Mitochondria were loaded with calcein and treated with 10 μM BID α6 14mer. Where noted, mitochondria were pretreated with 1 μM CsA. At the indicated time, mitochondria were pelleted by centrifugation and calcein in the pellet and in the supernatant was determined. The BID α6 14mer resulted in the efflux of mitochondrial matrix entrapped calcein indicating the onset of transient PT (FIG. 13).

Figure 14:
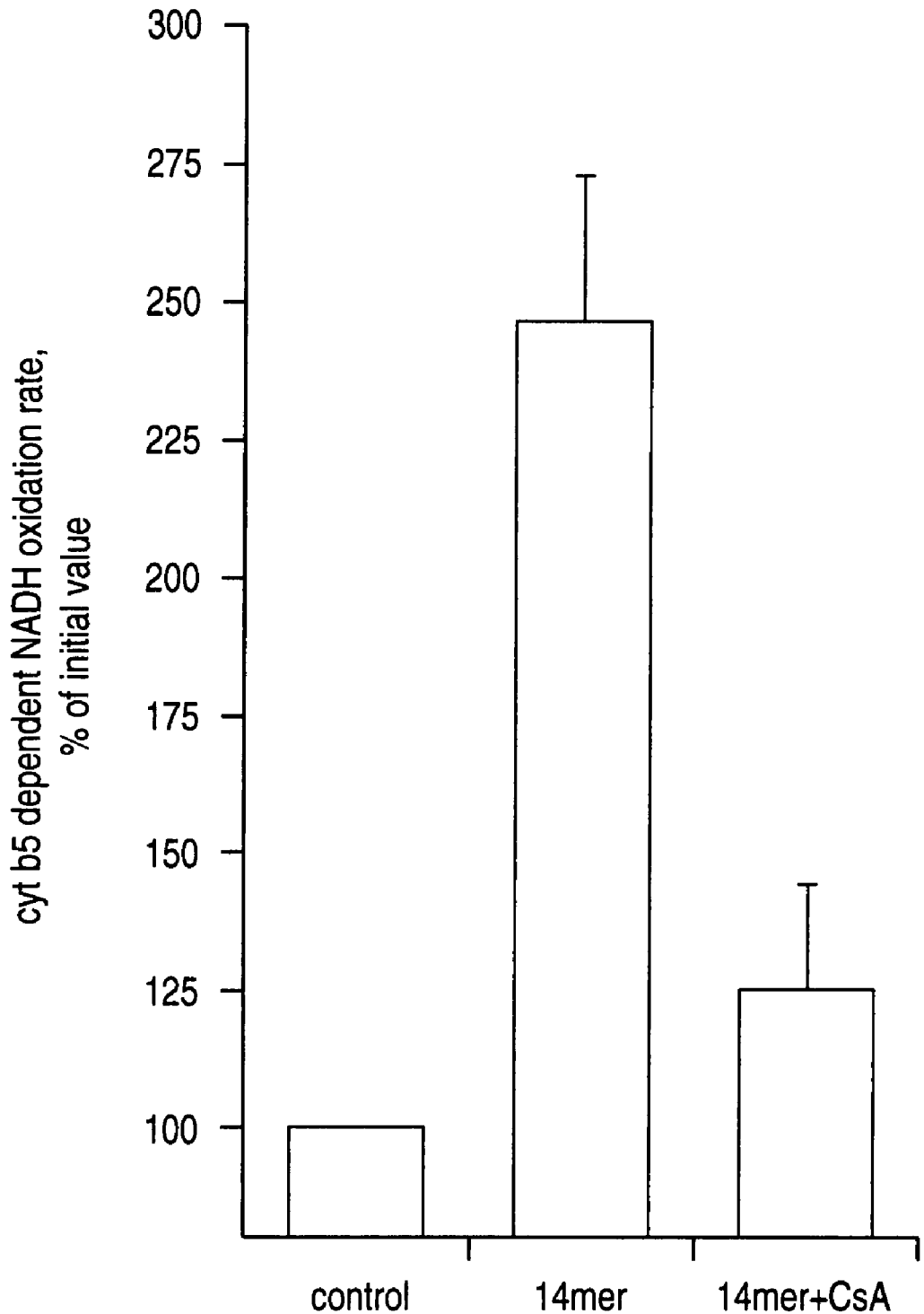
FIG. 14 is a bar graph showing that BID α6 14mer induces cytochrome c redistribution.

To determine if the BID α6 14mer (SEQ ID NO:1) could induce the mobilization of cytochrome c, mitochondria were incubated with 10 μM BID α6 14mer in the presence or in the absence of 1 μM CsA for 20 min. The cytochrome b5-dependent NADH oxidation rate was then determined. The results show that BID α6 14mer also induced the mobilization of cytochrome c as measured in the cytochrome b5-dependent NADH oxidation reaction, which was also sensitive to CsA (FIG. 14).

Figure 15:
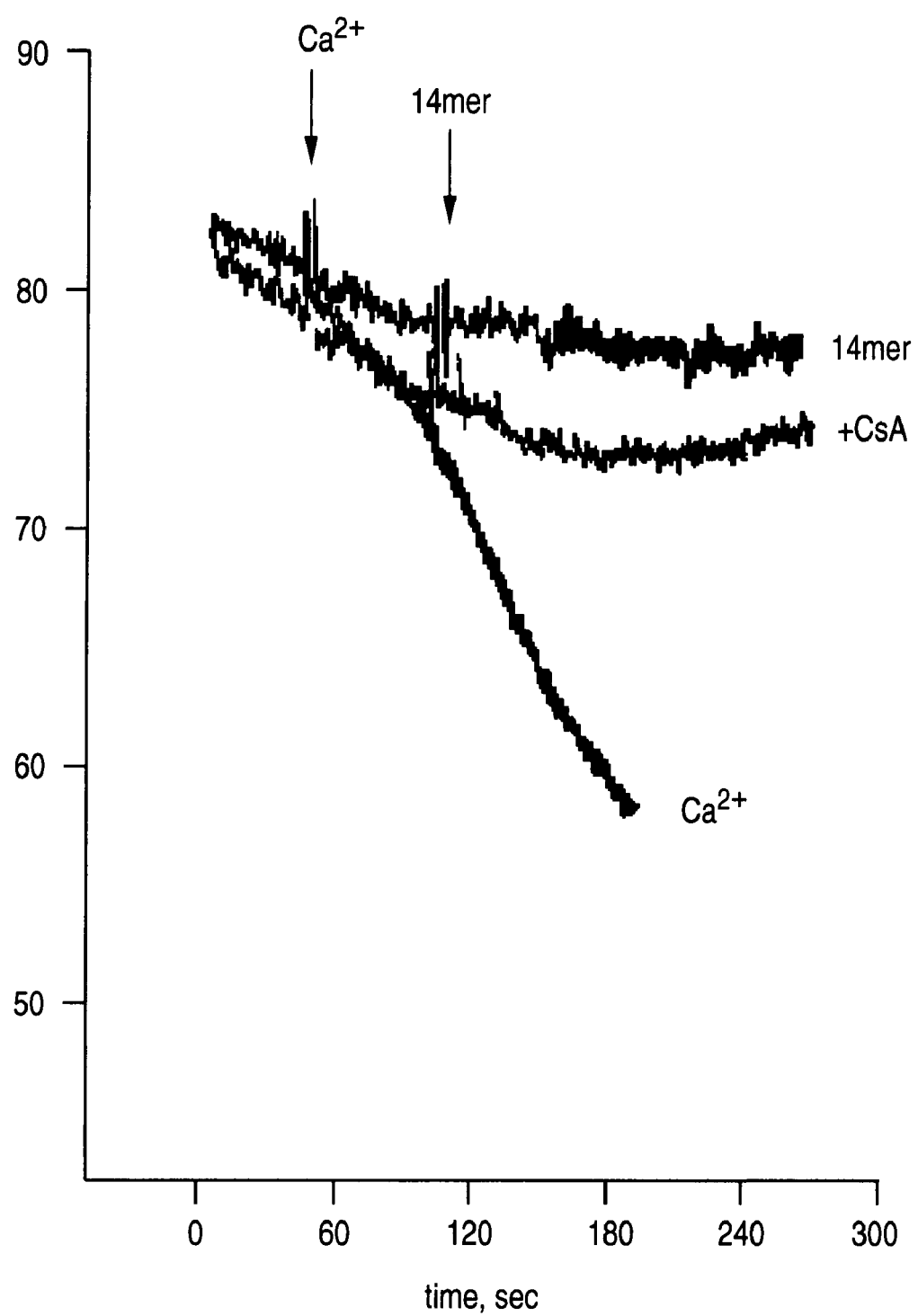
FIG. 15 is a line graph showing that BID α6 14mer does not induce mitochondrial swelling as measured by changes in light scattering at 545 nm.
Figure 16:
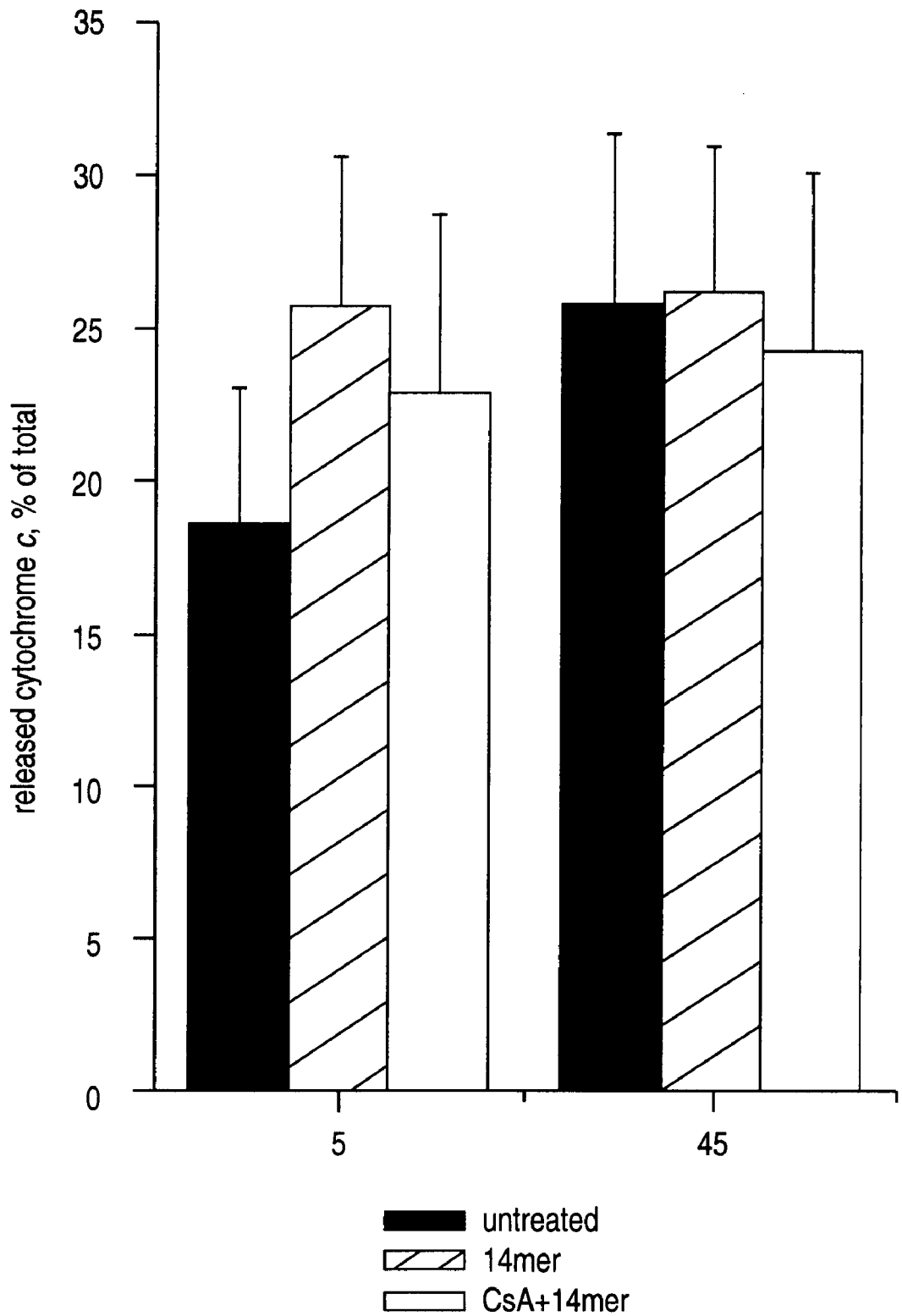
FIG. 16 is a bar graph showing that BID α6 14mer (SEQ ID NO:1) does not cause cytochrome c release across the outer membrane.

To determine if the BID α6 14mer (SEQ ID NO:1) induced mitochondrial swelling or release of cytochrome c across the mitochondrial outer membrane, mitochondria at 1 mg/ml were incubated in experimental buffer and, where indicated, 20 μM $Ca^{2+}$ and 10 μM 14mer were added. Where noted, mitochondria were preincubated with CsA. As a positive control, in the trace labeled as $Ca^{2+}$, maximal swelling was induced by 400 μM $Ca^{2+}$. Mitochondria were incubated with 10 μM 14mer in the presence or in the absence of 1 μM CsA. At the indicated time in minutes, mitochondria were pelleted by centrifugation and cytochrome c in the pellet and in the supernatant was determined. Results show that the BID α6 14mer did not induce swelling of mitochondria (FIG. 15) nor did it trigger the actual release of cytochrome c across the mitochondrial outer membrane (FIG. 16).

Figure 17:
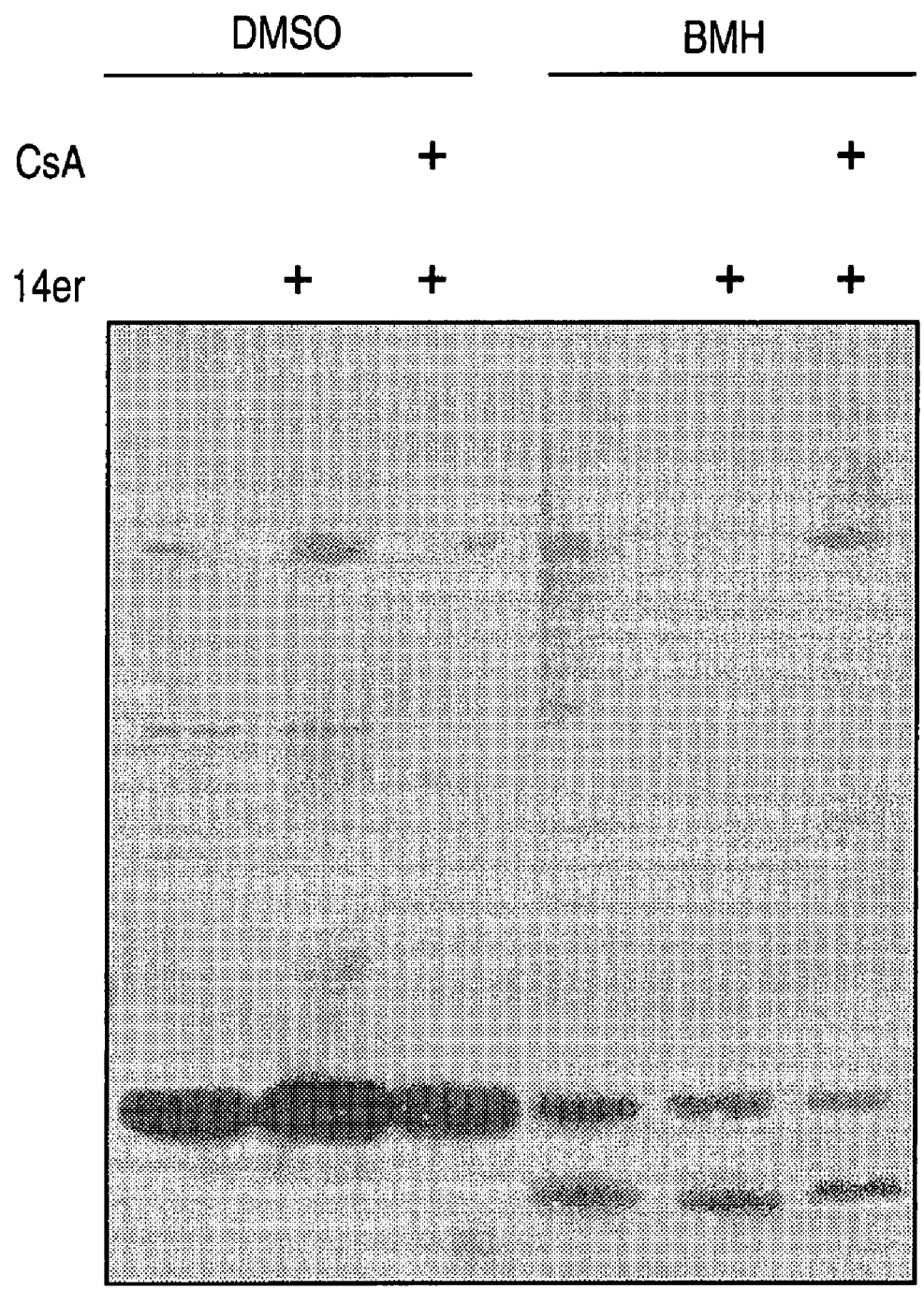
FIG. 17 is a photograph of a Western blot showing that BID α6 14mer does not induce BAK oligomerization.

To also determine if the BID α6 14mer (SEQ ID NO:1) modulated BAK oligomerization, mitochondria were incubated for 30 min with 10 μM BID α6 14mer in the presence or in the absence of 1 μM CsA. Crosslinking with BMH, SDS-PAGE and anti BAK immunoblotting was carried out. Consistent with similar results, the BID α6 14mer did not result in BAK oligomerization within the mitochondria (FIG. 17).

These data indicated that the tBID initiated, BAK-independent, CsA and Suramin sensitive pathway of mitochondrial inner membrane remodeling and transient PT could be recapitulated by a BID α6 14mer. The BID α6 mutein confirmed this region was critical for this pathway that clearly differs from the BH3 α3 helix dependent release of cytochrome c across the OM of mitochondria. This suggested that while the BH3 domain of tBID remained on the surface of the mitochondria, its α6 helix domain would be deeply inserted and located in the inner membrane.

Figure 18:
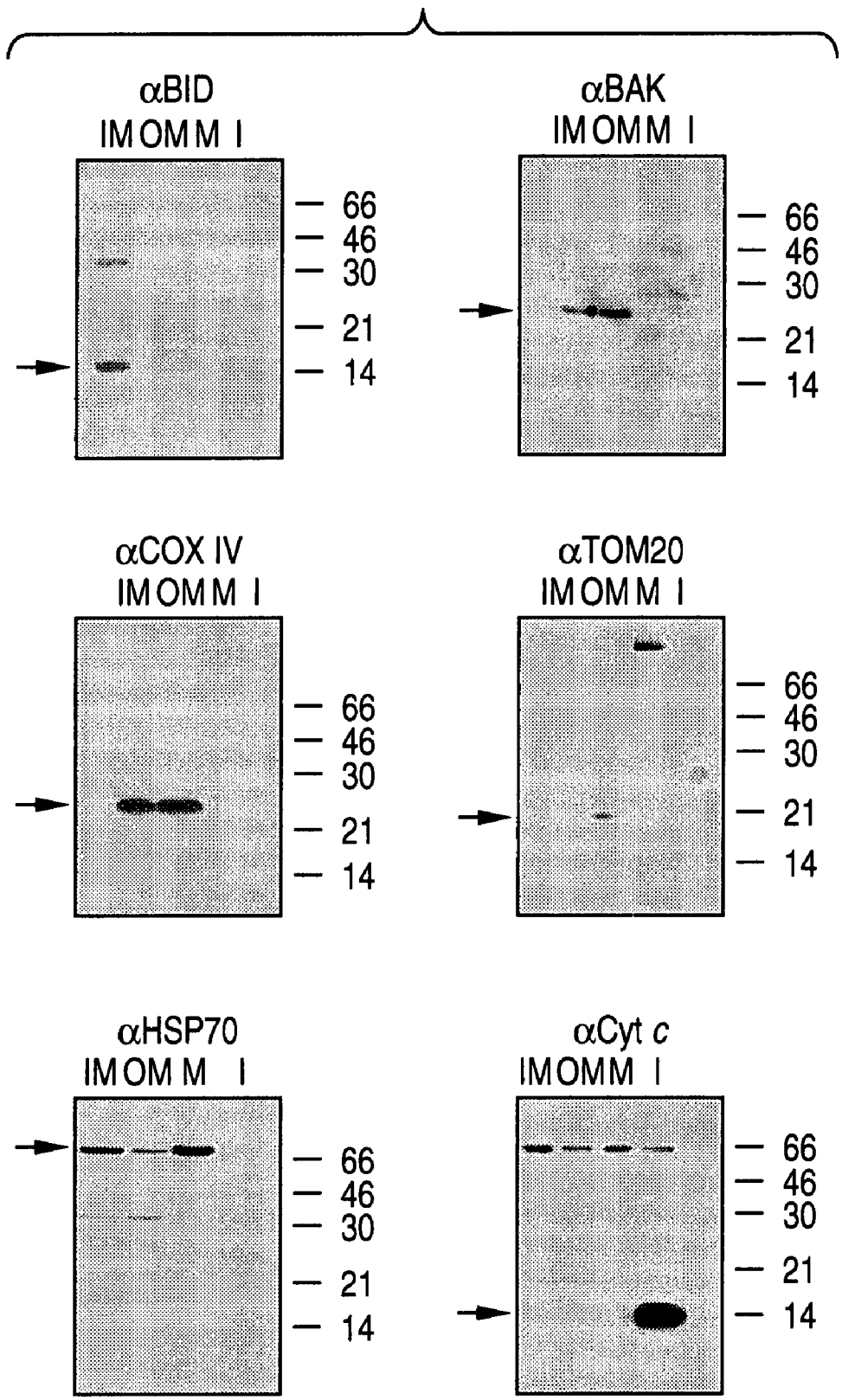
FIG. 18 is a photograph of a Western blot showing that tBID predominantly localizes at the inner mitochondrial membrane.

To assess the mitochondrial localization of these domains of tBID, 10 mg mitochondria were incubated with 320 pmol/mg tBID in experimental buffer for 30 min. and mitochondrial subfractions were isolated. Mitochondria were pelleted by centrifugation at 6000 g for 10 min at 4 C and then resuspended in a buffer containing 10 mM $KP_i$ pH 7.4 and incubated for 5 min on ice. Mitochondria were spun at 14000 g for 10 min at 4 C, and the resulting supernatant, corresponding to the IMS (I) was collected. The pellet was resuspended in 10 ml of 10 mM $KP_i$ pH 7.4. and 0.7 ml of a buffer containing 1.8 M sucrose, 2 mM ATP, 2 mM $MgSO_4$ was added. Mitochondria were allowed to contract for 5 min on ice and then were sonicated with 4 W pulses. Mitochondria were then layered on top of a 3 ml 1.18 M sucrose solution and a gradient was self generated by ultracentrifugation at 90000 g for 2 hrs at 4 C. Three different compartments were separated according to their different sedimentation coefficients: an upper soluble clear layer corresponding to the matrix (M) compartment, a yellow interphase corresponding to the outer membrane (OM), and a brownish pellet corresponding to the inner membrane (IM). Equal amounts of protein from each recovered fraction were subjected to 12% SDS-PAGE followed by immunoblotting with antibody against BID, BAK and markers of the mitochondrial subcompartments: HSP75 (1:1000) for the M, cytochrome c for the inner membrane space (I), cytochrome c oxidase IV for the IM and TOM20 for the OM. Submitochondrial fractionation of targeted tBID indicated that it did indeed localize to the inner mitochondrial membrane fraction (FIG. 18).

The CsA and suramin inhibition of the BID α6 helix mediated remodeling process indicated that BID would interact with other mitochondrial membrane based complexes to mediate this pathway. Downstream mediators include the participation of cyclophilin D, the only known mitochondrial target for CsA. In addition, a suramin responsive G protein is implicated in a BID protein complex that would mediate this pathway.

To assess the presence or absence of other mediators participating in this pathway, mitochondria (20 mg protein) were lysed for 30 min on ice in 1 ml of a buffer containing 150 mM NaCl, 10 mM Tris pH 7.4, 0.2 mM phenylmethylsulfonyl fluoride, 0.8 mM benzamidine, and 1.0% Triton X100. The lysate was spun at 55,000×g for 45 min and the supernatant was recovered and incubated at 4° C. with an empty Agarose resin for 4 hrs. The flow-through from the resin was collected and loaded onto an agarose resin coupled to p7/p15 caspase 8 cleaved BID (0.8 mg BID/ml resin volume) and incubated for 12 hrs at 4° C. The resin was washed sequentially with 10 bed volumes of lysis buffer, followed by 5 volumes of the same lysis buffer containing 0.5 M NaCl, and then by a final wash with 10 bed volumes of lysis buffer. The flow-through (W) was collected. Bound proteins were eluted with 10 μM BID α6 14mer (SEQ ID NO:1) dissolved in 5 bed volumes of the respective lysis buffer, and 5 elution fractions were collected. Fractions were immediately concentrated 10-fold by TCA precipitation. Proteins were then separated on a 4-12% SDS-PAGE gradient gel and silver stained. Lane W contains the proteins eluted by the 0.5 M NaCl wash, and lanes 1-5 represent proteins from the corresponding five peptide-eluted fractions. A BID affinity column purification of mitochondrial lysates followed by specific elution by a BID α6 peptide revealed a BID associated protein complex (FIG. 19). These constitute BID complexed proteins that mediate the program of mitochondrial remodeling and subsequent dysfunction. The identity of each member may be determined by Mass spectrometry based peptide sequencing.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated BID mutein polypeptide comprising the amino acid sequence of SEQ ID NO: 8 or 9, wherein said BID-mutein contacts a cell and decreases mitochondrial inner membrane remodeling, decreases cytochrome c mobilization, or decreases apoptosis.

2. An isolated polypeptide comprising the amino acid sequence selected from the group consisting of SEQ ID NO: 8 and 9.

3. The isolated polypeptide of claim 1 or 2, wherein said polypeptide does not dimerize with BAX, BCL-2 or BCL-X.

4. An isolated BID mutein polypeptide of less than or equal to 50 amino acids in length comprising the sequence of SEQ ID NO: 8 or 9.

* * * * *

SEQUENCE LISTING

<160> NUMBER OF SEQ ID NOS: 11

<210> SEQ ID NO 1
<211> LENGTH: 14
<212> TYPE: PRT
<213> ORGANISM: Homo sapiens
<220> FEATURE:
<221> NAME/KEY: VARIANT
<222> LOCATION: (1)
<223> OTHER INFORMATION: Wherein Xaa is any amino acid as defined in the
      specification.
<220> FEATURE:
<221> NAME/KEY: VARIANT
<222> LOCATION: (4)..(7)
<223> OTHER INFORMATION: Wherein Xaa is any amino acid as defined in the
      specification.

<400> SEQUENCE: 1

Xaa Met Leu Xaa Xaa Xaa Xaa Leu Leu Ala Lys Lys Val Ala
 1               5                  10

<210> SEQ ID NO 2
<211> LENGTH: 14
<212> TYPE: PRT
<213> ORGANISM: Homo sapiens

<400> SEQUENCE: 2

Thr Met Leu Val Leu Ala Leu Leu Ala Lys Lys Val Ala
 1               5                  10

<210> SEQ ID NO 3
<211> LENGTH: 14
<212> TYPE: PRT
<213> ORGANISM: Homo sapiens

<400> SEQUENCE: 3

Ala Met Leu Ile Met Thr Met Leu Leu Ala Lys Lys Val Ala
 1               5                  10

<210> SEQ ID NO 4
<211> LENGTH: 195
<212> TYPE: PRT
<213> ORGANISM: Homo sapiens

<400> SEQUENCE: 4

Met Asp Cys Glu Val Asn Asn Gly Ser Ser Leu Arg Asp Glu Cys Ile
 1               5                  10                  15

Thr Asn Leu Leu Val Phe Gly Phe Leu Gln Ser Cys Ser Asp Asn Ser
                20                  25                  30

Phe Arg Arg Glu Leu Asp Ala Leu Gly His Glu Leu Pro Val Leu Ala
            35                  40                  45

Pro Gln Trp Glu Gly Tyr Asp Glu Leu Gln Thr Asp Gly Asn Arg Ser
        50                  55                  60

Ser His Ser Arg Leu Gly Arg Ile Glu Ala Asp Ser Glu Ser Gln Glu
 65                  70                  75                  80

Asp Ile Ile Arg Asn Ile Ala Arg His Leu Ala Gln Val Gly Asp Ser
                85                  90                  95

Met Asp Arg Ser Ile Pro Pro Gly Leu Val Asn Gly Leu Ala Leu Gln
            100                 105                 110

Leu Arg Asn Thr Ser Arg Ser Glu Glu Asp Arg Asn Arg Asp Leu Ala
        115                 120                 125

```
Thr Ala Leu Glu Gln Leu Leu Gln Ala Tyr Pro Arg Asp Met Glu Lys
    130                 135                 140

Glu Lys Thr Met Leu Val Leu Ala Leu Leu Leu Ala Lys Lys Val Ala
145                 150                 155                 160

Ser His Thr Pro Ser Leu Leu Arg Asp Val Phe His Thr Thr Val Asn
                165                 170                 175

Phe Ile Asn Gln Asn Leu Arg Thr Tyr Val Arg Ser Leu Ala Arg Asn
                180                 185                 190

Gly Met Asp
        195

<210> SEQ ID NO 5
<211> LENGTH: 196
<212> TYPE: PRT
<213> ORGANISM: Rattus norvegicus

<400> SEQUENCE: 5

Met Asp Ser Glu Val Ser Asn Gly Ser Gly Leu Gly Ala Glu His Ile
1               5                   10                  15

Thr Asn Leu Leu Val Phe Gly Phe Leu Arg Asn Asn Asp Arg Asp Phe
                20                  25                  30

His Gln Glu Leu Glu Val Leu Gly Gln Glu Leu Pro Val Gln Val Tyr
            35                  40                  45

Leu Glu Gly Asp Arg Glu Asp Glu Leu Gln Thr Asp Gly Ser Arg Ala
    50                  55                  60

Ser Arg Ser Phe Tyr His Gly Arg Ile Glu Pro Asp Ser Glu Ser Gln
65                  70                  75                  80

Asp Glu Val Ile His Asn Ile Ala Arg His Leu Ala Gln Ala Gly Asp
                85                  90                  95

Glu Leu Asp His Ser Ile Gln Pro Thr Leu Val Arg Gln Leu Ala Ala
            100                 105                 110

Gln Phe Met Asn Gly Ser Leu Ser Glu Glu Asp Lys Arg Asn Cys Leu
        115                 120                 125

Ala Lys Ala Leu Asp Glu Val Lys Thr Ser Phe Pro Arg Asp Met Glu
    130                 135                 140

Asn Asp Lys Ala Met Leu Ile Met Thr Met Leu Leu Ala Lys Lys Val
145                 150                 155                 160

Ala Ser His Ala Pro Ser Leu Arg Asp Val Phe Arg Thr Thr Val
                165                 170                 175

Asn Phe Ile Asn Gln Asn Leu Phe Ser Tyr Val Arg Asp Leu Val Arg
                180                 185                 190

Asn Glu Met Asp
        195

<210> SEQ ID NO 6
<211> LENGTH: 195
<212> TYPE: PRT
<213> ORGANISM: Mus musculus

<400> SEQUENCE: 6

Met Asp Ser Glu Val Ser Asn Gly Ser Gly Leu Gly Ala Lys His Ile
1               5                   10                  15

Thr Asp Leu Leu Val Phe Gly Phe Leu Gln Ser Ser Gly Cys Thr Arg
                20                  25                  30

Gln Glu Leu Glu Val Leu Gly Arg Glu Leu Pro Val Gln Ala Tyr Trp
            35                  40                  45
```

```
Glu Ala Asp Leu Glu Asp Glu Leu Gln Thr Asp Gly Ser Gln Ala Ser
        50                  55                  60
Arg Ser Phe Asn Gln Gly Arg Ile Glu Pro Asp Ser Glu Ser Gln Glu
 65                  70                  75                  80
Glu Ile Ile His Asn Ile Ala Arg His Leu Ala Gln Ile Gly Asp Glu
                85                  90                  95
Met Asp His Asn Ile Gln Pro Thr Leu Val Arg Gln Leu Ala Ala Gln
            100                 105                 110
Phe Met Asn Gly Ser Leu Ser Glu Glu Asp Lys Arg Asn Cys Leu Ala
        115                 120                 125
Lys Ala Leu Asp Glu Val Lys Thr Ala Phe Pro Arg Asp Met Glu Asn
130                 135                 140
Asp Lys Ala Met Leu Ile Met Thr Met Leu Leu Ala Lys Lys Val Ala
145                 150                 155                 160
Ser His Ala Pro Ser Leu Leu Arg Asp Val Phe His Thr Thr Val Asn
                165                 170                 175
Phe Ile Asn Gln Asn Leu Phe Ser Tyr Val Arg Asn Leu Val Arg Asn
            180                 185                 190
Glu Met Asp
        195

<210> SEQ ID NO 7
<211> LENGTH: 14
<212> TYPE: PRT
<213> ORGANISM: Homo sapiens
<220> FEATURE:
<221> NAME/KEY: VARIANT
<222> LOCATION: (1)
<223> OTHER INFORMATION: Wherein Xaa is any amino acid as defined in the
      specification.
<220> FEATURE:
<221> NAME/KEY: VARIANT
<222> LOCATION: (4)..(7)
<223> OTHER INFORMATION: Wherein Xaa is any amino acid as defined in the
      specification.

<400> SEQUENCE: 7

Xaa Met Leu Xaa Xaa Xaa Xaa Leu Leu Ala Ala Ala Val Ala
 1               5                  10

<210> SEQ ID NO 8
<211> LENGTH: 14
<212> TYPE: PRT
<213> ORGANISM: Homo sapiens

<400> SEQUENCE: 8

Ala Met Leu Ile Met Thr Met Leu Leu Ala Ala Ala Val Ala
 1               5                  10

<210> SEQ ID NO 9
<211> LENGTH: 14
<212> TYPE: PRT
<213> ORGANISM: Homo sapiens

<400> SEQUENCE: 9

Thr Met Leu Val Leu Ala Leu Leu Leu Ala Ala Ala Val Ala
 1               5                  10

<210> SEQ ID NO 10
<211> LENGTH: 20
<212> TYPE: PRT
<213> ORGANISM: Homo sapiens
```

```
<400> SEQUENCE: 10

Met Glu Asn Asp Lys Ala Met Leu Ile Met Thr Met Leu Leu Ala Lys
  1               5                  10                  15

Lys Val Ala Ser
             20

<210> SEQ ID NO 11
<211> LENGTH: 14
<212> TYPE: PRT
<213> ORGANISM: Homo sapiens

<400> SEQUENCE: 11

Ile Asn Leu Lys Ala Leu Ala Ala Leu Ala Lys Lys Ile Leu
  1               5                  10
```